(12) United States Patent
Stauffer

(10) Patent No.: US 12,251,848 B2
(45) Date of Patent: *Mar. 18, 2025

(54) SELF-PROPELLED DRIVE AND CUTTER USING SAME

(71) Applicant: Jonathan Stauffer, Colora, MD (US)

(72) Inventor: Jonathan Stauffer, Colora, MD (US)

( * ) Notice: Subject to any disclaimer, the term of this patent is extended or adjusted under 35 U.S.C. 154(b) by 345 days.

This patent is subject to a terminal disclaimer.

(21) Appl. No.: 17/952,720

(22) Filed: Sep. 26, 2022

(65) Prior Publication Data

US 2023/0012889 A1    Jan. 19, 2023

Related U.S. Application Data

(63) Continuation-in-part of application No. 16/775,388, filed on Jan. 29, 2020, now Pat. No. 11,453,139.

(60) Provisional application No. 62/798,043, filed on Jan. 29, 2019.

(51) Int. Cl.
    *B26B 27/00* (2006.01)
    *A61F 15/02* (2006.01)
    *B26B 29/06* (2006.01)

(52) U.S. Cl.
    CPC .............. *B26B 27/00* (2013.01); *A61F 15/02* (2013.01); *B26B 29/06* (2013.01)

(58) Field of Classification Search
    CPC ......... B26B 27/00; B26B 27/05; B26B 29/02; B26B 29/06; A61F 15/02
    USPC ......... 30/280–282, 286, 289, 294, 314, 378, 30/500
    See application file for complete search history.

(56) References Cited

U.S. PATENT DOCUMENTS

| | | |
|---|---|---|
| 1,269,373 A | 6/1918 | Bergeron |
| 1,876,337 A | 9/1932 | Mead |
| 2,084,488 A | 6/1935 | Heller |
| 2,492,156 A | 12/1949 | Kupjack |
| 2,522,006 A | 9/1950 | Wilcox |
| 3,528,175 A | 9/1970 | Rich |
| 3,670,412 A | 6/1972 | Cunningham |
| 3,736,659 A | 6/1973 | McLean |
| 4,081,906 A | 4/1978 | Sigler |
| 4,215,451 A | 8/1980 | Wikoff |

(Continued)

FOREIGN PATENT DOCUMENTS

WO    2015079226 A1    6/2015

OTHER PUBLICATIONS

International Search Authority, USPTO, International Search Report and Written Opinion, PCT/US2022/044706, Mailed on Feb. 9, 2023.

*Primary Examiner* — Jason Daniel Prone

(57) ABSTRACT

A self-propelled cutter has a gear assembly to provide both downward and forward force on a material to be cut. A gear assembly includes a drive input gear that engages with a transfer gear and propulsion gear engaged with the transfer gear by a lever arm. The drive gear and transfer gear are coupled and fixed to the cutter body but the propulsion gear rotates about the transfer gear via the lever arm. This gear assembly enables the propulsion gear to move as required to provide both downward and forward force on a material to be cut, such as a cast. A self-propelled cutter may have a drive input that is coupled with a drive input device, such as a crank or an electric motor. A cutter may have a first gear assembly on a first side of the cutter body and a second gear assembly on a second side.

17 Claims, 20 Drawing Sheets

(56) References Cited

U.S. PATENT DOCUMENTS

| | | | |
|---|---|---|---|
| 4,385,440 | A | 5/1983 | Webb |
| 4,611,585 | A | 9/1986 | Steidle |
| 5,020,226 | A | 6/1991 | Chabbert |
| 5,485,676 | A | 1/1996 | Terhorst |
| 5,590,471 | A | 1/1997 | Wiezenthal |
| 5,659,961 | A | 8/1997 | Boerbrink |
| 8,414,595 | B2 | 4/2013 | Baker |
| 8,453,546 | B2 | 6/2013 | Ross |
| 11,453,139 | B1 * | 9/2022 | Stauffer ................. B26B 27/00 |
| 2003/0065334 | A1 | 4/2003 | Hobgood et al. |
| 2010/0024223 | A1 | 2/2010 | Lehman et al. |
| 2010/0146797 | A1 | 6/2010 | Dreher |
| 2011/0270263 | A1 | 11/2011 | Baker |

* cited by examiner

SELF-PROPELLED DRIVE AND CUTTER USING SAME

CROSS REFERENCE TO RELATED APPLICATIONS

This application is a continuation in part of U.S. patent application Ser. No. 16/775,388, filed on Jan. 29, 2020 and issued as U.S. Pat. No. 11,453,139 on Sep. 27, 2022, which claims the benefit of U.S. provisional application No. 62/798,043, filed on Jan. 29, 2019, entitled Self Propelled drive and Cutter Using Same, the entirety of which is hereby incorporated by reference herein.

BACKGROUND OF THE INVENTION

Field of the Invention

The invention relates to a self-propelled cutter having a fixed blade and gear assembly to drive the cutter across a material to be cut, such as a cast.

Background

Self-propelled cutters often have moving blades that rotate or vibrate to cut. This can be dangerous when the material to be cut is a cast. Rotating blades can easily cut the patient, adding significant risk to their use, and as such must be guarded carefully. Vibrating blades generate excessive noise, dust, and heat. The noise often scares younger patients. The dust must be captured and removed, and in some cases, the heat generated can result in burns to the patient. Fixed blade cutters typically require manual force to cut through the material.

SUMMARY OF THE INVENTION

The invention is directed to a self-propelled cutter having an arrangement of gears to provide both downward and forward force on a material to be cut to propel the cutter across the material. An exemplary gear assembly includes a drive input gear that engages with a transfer gear and propulsion gear engaged with the transfer gear by a lever arm. In an exemplary embodiment, the drive gear and transfer gear are coupled and fixed to the cutter body but the propulsion gear rotates about the transfer gear via the lever arm. This exemplary gear assembly enables the propulsion gear to move as required to provide both downward and forward force on a material to be cut, such as a cast. In some embodiments, the transfer gear may be directly coupled with the drive input, thereby eliminating the need for the drive gear.

An exemplary self-propelled cutter has a drive input that is coupled with the drive gear or gears and a drive input device, such as a crank or electric motor, may be coupled with the drive input to rotate the drive gear and thereby drive the other gears in the gear assembly. In an exemplary embodiment, the drive input extends out of one of the first or second sides of the cutter body and the drive gear and transfer gear have rotational axes that are parallel. In an exemplary embodiment, the drive input extends out the front or back of the cutter body and the drive gear is a worm gear having a rotational axis that is orthogonal to the transfer gear's rotational axis. An exemplary drive gear has engagement teeth that engage with engagement teeth of the transfer gear.

An exemplary propulsion gear is configured at an offset angle to a vertical axis and trails the transfer gear, whereby the rotational axis of the propulsion gear is located back from the rotational axis of the transfer gear with respect to the cutter body. The offset angle may be about 0 degrees or more, about 15 degrees or more, about 25 degrees or more, about 35 degrees or more, about 90 degrees or less, about 75 degrees of less, about 60 degrees or less, or any range between and including the offset angles provided such as from about 0 degrees to about 60 degrees. This offset angle may be limited by stops, a front-stop and a back-stop, or springs, that are part of or coupled to the cutter body.

An exemplary propulsion gear has engagement teeth that engage with engagement teeth of the transfer gear. An exemplary propulsion gear has a tread that makes contact with the material to be cut and is an outermost radial extension from the axis of rotation. An exemplary tread may be the engagement teeth of the propulsion gear or a separate ring or disc that is coupled with the propulsion gear and extends out more radially than the engagement teeth of the propulsion gear. The tread may engage with the material to be cut and thereby keep the engagement teeth of the propulsion gear free of debris. An exemplary tread may be detachably attachable which may allow a user to change the type of tread used to accommodate the material to be cut.

An exemplary self-propelled cutter has a first gear assembly on a first side of the cutter body and a second gear assembly on a second side of the cutter body. A first side of the cutter body is the side having the drive input. A drive input may be configured to drive both a first and second drive gear and thereby drive both gear assemblies. Two treads may enable the cutter to be propelled evenly across the material with respect to the central blade and may be preferred. A self-propelled cutter with a tread or engagement teeth only on one side of the blade may have a tendency to walk away from the side having the tread. In an exemplary embodiment, a self-propelled cutter has one gear assembly but has a propulsion gear assembly with two treads, whereby the cutter body has a propulsion gear body recess to accommodate an extension of the propulsion gear from the first side to the second side of the cutter body. A second tread may be coupled to this propulsion gear extension and provide uniform propulsion on either side of the blade.

An exemplary self-propelled cutter comprises a blade that is fixed and therefore not a rotating or reciprocating blade. The blade may be coupled to a blade assembly and may be detachably attached to the cutter body. A blade fastener may be coupled with the cutter body and allow a user to disengage the blade or blade assembly to change out the blade as required. The blade may be a razor blade and may be a common commercially available type of blade and the blade assembly may be configured to receive the blade. A blade, as used herein, is any cutting implement and may be a fixed cutting implement having a sharp cutting surface and the blade may be detachably attachable to the foot or be an integral part of the foot, such as a sharp edge of the foot.

An exemplary self-propelled cutter comprises a foot that is configured below the blade and guides the material to be cut up and over the blade. The material to be cut may be captured and pinched between the foot and the propulsion gear or tread, and the cutter propels itself along the material to be cut. Therefore, an exemplary foot extends outward from the blade. An exemplary foot extends forward the blade and protects a user from exposure to the blade. An exemplary foot has a width that is about 30 mm or less, about 20 mm or less, about 10 mm or less, about 5 mm or less, about 4 mm or less, about 3 mm or less and any range between and including the foot widths provided. It is desirable to reduce the friction required to propel the self-propelled cutter over material to be cut and a wider foot may increase the friction.

The foot may be configured to pivot to allow thicker material to deflect the foot to enable the thicker material to pass between the cutter body and the foot. The foot may be coupled to a foot pivot plate that is configured to pivot about a foot pivot. The foot pivot may be configured more forward than the foot, wherein the trailing end of the foot is further away from the foot pivot than the leading edge of the foot. A spring may be coupled to the foot pivot plate to apply a force on the foot pivot plate, which creates a moment force about the foot pivot to cause the foot to rotate about the foot pivot. The foot spring may be configured more proximal to the back of the cutter body than the foot and may create an upward force, or force to pull the pivot foot plate up toward the top of the cutter body. In this way, thick material can force the foot to pivot down and away from the cutter body and then after the material is passed over the foot and cut, the foot will be pulled back up to a stop position, a position dictated by a stop to prevent the foot pivot plate from rotating further up toward the top of the cutter body. The foot pivot may form a foot pivot axis through the cutter body that is more forward the rotation axis of the propulsion gear(s) and also, more forward the rotational axis of the transfer gear(s).

A foot spring may comprise an elastomeric material, such as silicone, urethane or rubber, that produces a force to pull the foot pivot plate upward about the foot pivot, or a coiled spring that may be made of metal, for example.

An exemplary self-propelled cutter may have a first gear assembly on a first side of the cutter body and a second gear assembly on a second side of the cutter body, distal the drive input from a drive input device. A first gear assembly may include a first transfer gear that is meshed with a first propulsion gear. The first transfer gear may be meshed directly with a drive gear or may be coupled with an interface transfer gear, wherein the interface transfer gear meshes with the drive gear. The drive gear may be coupled to the drive input. The interface transfer gear and the first drive gear may be coupled by an axle and this axle may extend through the cutter body to the second side of the cutter body, where a second transfer gear is coupled to this axle. The first transfer gear and second transfer gear may therefore rotate about the same rotational axis, or around this common axle, a transfer gear axle. Each of the transfer gears may mesh with a respective propulsion gear and for stability the two propulsion gears may rotate about the same propulsion axis, and around a common propulsion axle that extends through the cutter body. This exemplary self-propelled cutter therefore has two common rotational axes, a transfer gear rotational axis and a propulsion gear rotational axis.

The combination of the dual sided tread configured on opposing sides of the cutter body and the foot spring pulling the foot up toward the cutter body provides effective force between the foot and the blade to ensure the material is cut while the tread effectively translates the material over the foot and blade, as indicated by the two bold arrows proximal the trailing end of the foot.

It is to be understood that this drive mechanism and particularly the orientation of the drive gear with respect to the transfer gear, whereby the drive gear rotates about the transfer gear, could be used on any number of mechanical devices requiring driving of an object, such as along a plane or direction. Such devices may include any type of self-propelled object including a vehicle, lawn equipment, or toy, or devices that propel an object such as a tool, a table or band saw, and the like.

An exemplary self-propelled cutter may be portable in size such that it can be carried easily by a single person and may have a width and/or length of about 30 cm or less, about 20 cm or less, about 10 cm or less and any range between and including the length values provided.

Self-propelled, as used herein, describes a tread that pulls the material to be cut through the foot of the cutter; a self-propelled cutter may have a manual drive input or a motorized drive input.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
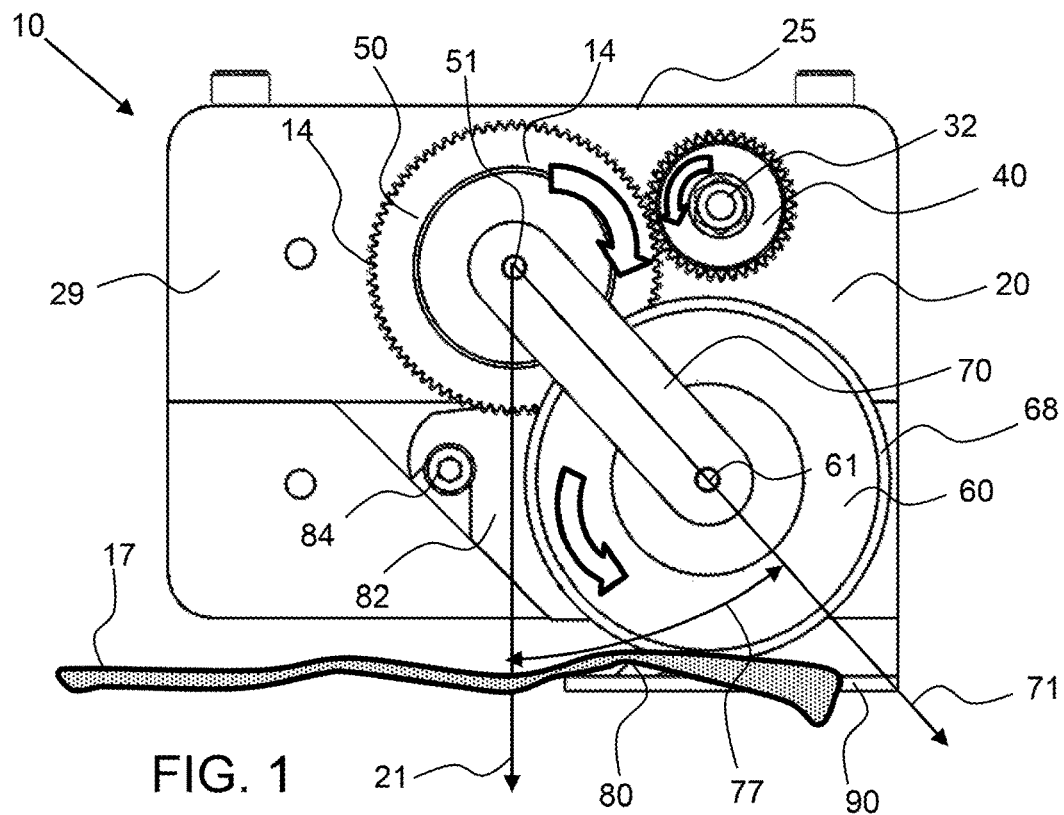
FIG. 1 shows a second side of an exemplary self-propelled cutter having a drive gear engaged with a transfer gear and the transfer engaged with a propulsion gear by a lever arm.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary self-propelled cutter 10 is in an upright position and has a drive assembly 14 including a drive gear 40 engaged with a transfer gear 50 and the transfer engaged with a propulsion gear 60 by a lever arm 70. The lever arm 70 enables the propulsion gear 60 to rotate about the transfer gear 50 as required to drive the material through the cutter 10. As indicated by the bold arrows, the propulsion gear 60 is driven indirectly by the drive gear 40, which is driven by the drive input extension 32 that extends through the cutter body 20. The propulsion gear 60 provides downward and horizontal forces on the material 17 to be cut. The rotational axis 61 of the propulsion gear 60 and lever arm axis 71 are configured at an offset angle 77 from the vertical axis 21, extending though the rotation axis 51 of the transfer gear 50. This offset angle and ability to pivot about the transfer gear 50 enables the propulsion gear 60 to self-regulate downward and horizontal forces on a material moving through the cutter 10. The engagement teeth of the propulsion gear 60 may grip the material to be cut and pull it through the cutter 10. The propulsion gear may have a tread 68 that extends around the engaging propulsion gear 60, wherein the tread extends radially outward beyond engagement teeth of the propulsion gear 60. The tread may provide better grip on the material to be cut 17 and may prevent debris from getting into the propulsion gear 60. An exemplary blade 80 is detachably attached to the cutter body 20 by a blade fastener 84, such as a bolt. The blade assembly 82 may then be removed and the blade may be exchanged for a new blade. A foot 90 is configured to extend under the material to be cut 17 and direct it over the fixed blade 80.

Figure 2:
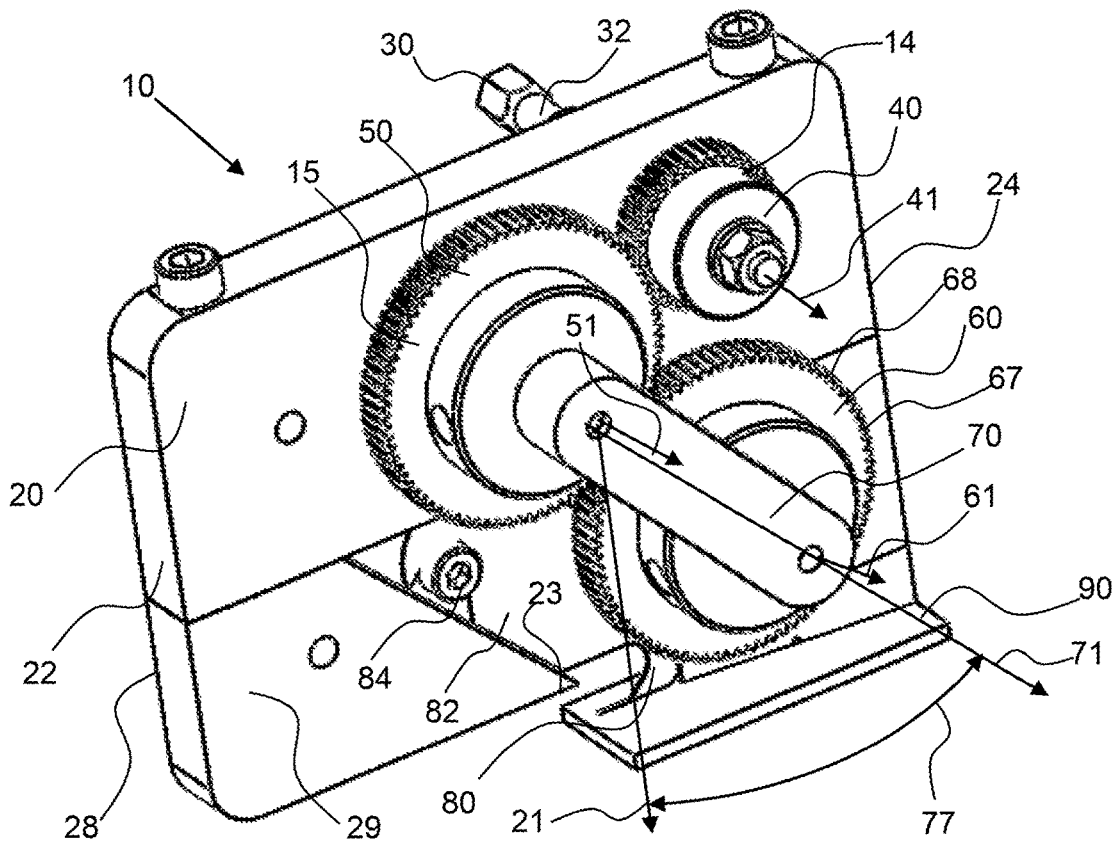
FIG. 2 shows a perspective view of a second side of an exemplary self-propelled cutter having a drive gear engaged with a transfer gear and the transfer engaged with a propulsion gear by a lever arm; the drive input is on the opposing side.

As shown in FIG. 2, an exemplary self-propelled cutter 10 is shown. The drive input 30 is shown on the first side 28 of the cutter body 20. A first set of gears, or gear assembly 15, is shown on the second side 29 of the cutter body 20. The rotational axis 41 of the drive gear 40 and the rotational axis 51 of the transfer gear 50 are shown. The drive input extension 32 extends from the drive input 30, through the cutter body 20 to the second side 29 of the cutter body 20. The rotational axis 61 of the propulsion gear 60 will move in an arc about the rotation axis 51 of the transfer gear 50, due to the lever arm 70 linkage. The lever arm 70 holds the transfer gear 50 and propulsion gear 60 in engagement with each other. The foot 90 extending in front of the fixed blade 80 is more clearly seen in this view. The propulsion gear 60 can rotate between the front-stop 23 and back-stop.

Figure 3:
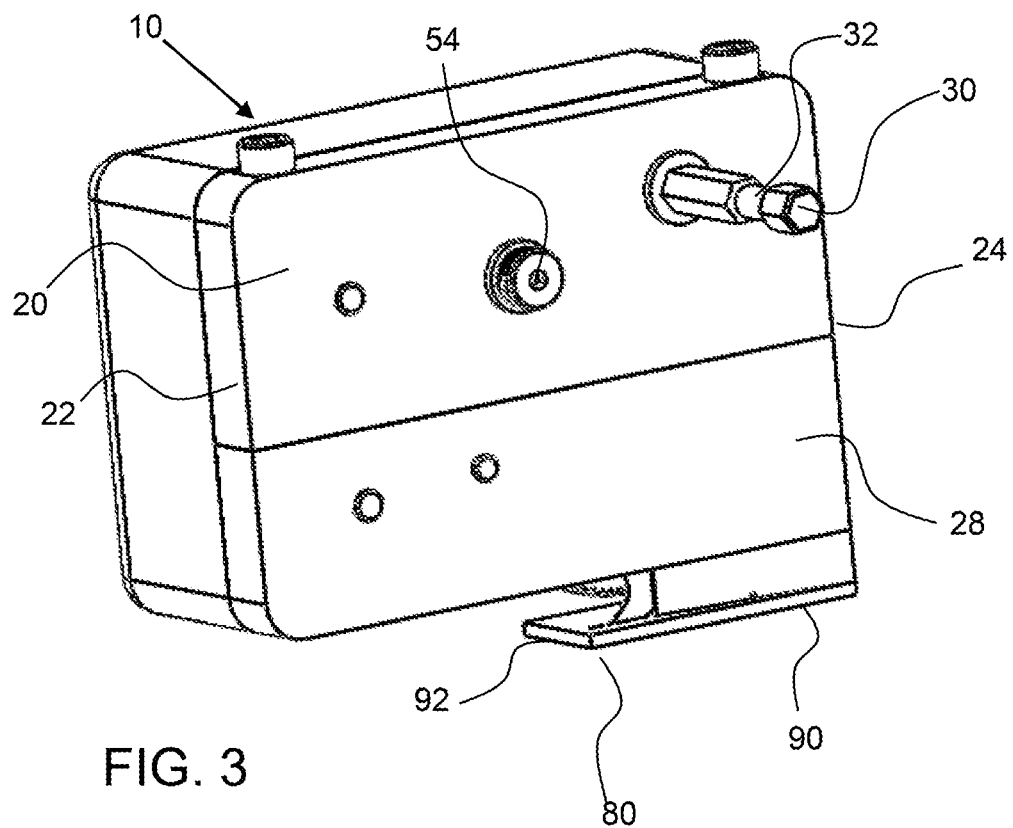
FIG. 3 shows a perspective view of a first side of an exemplary self-propelled cutter having a drive input extension extending to the first side to drive the drive gear.
Figure 4:
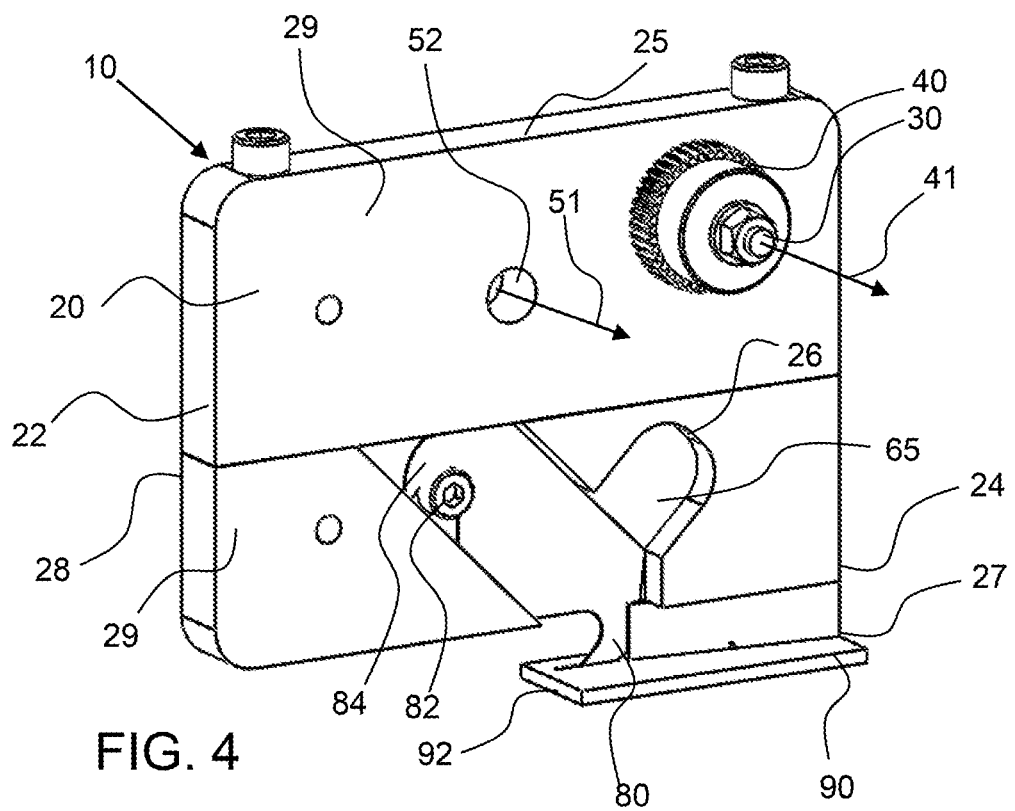
FIG. 4 shows a perspective view of a first side of an exemplary self-propelled cutter having a drive gear coupled to the drive input extension.

Referring now to FIGS. 3 and 4, an exemplary self-propelled cutter 10 has a drive input 30 comprising a drive input extension 32 extending from the first side 28 to the second side 29 to drive the drive gear 40; shown attached to the drive input extension in FIG. 4. The transfer gear 50 is coupled with a transfer gear bearing 54 that is coupled to the cutter body 20 via a transfer gear mount aperture 52. As shown in FIG. 4, the cutter body 20 may have a propulsion gear body recess 65 to allow a propulsion gear extension to extend across or through the cutter body 20 to couple with a second tread. Note that the back end of this recess 65 provides the back-stop 26 to prevent the propulsion gear 60 from rotating too far back about the transfer gear. The cutter body 20 has a length from the front 22 to the back 24 and a height from the bottom 27 to the top 25. As shown in FIG. 3, the drive input is configured on a side that may be conducive for a left handed person to manipulate a hand operated input, such as a handle.

Figure 5:
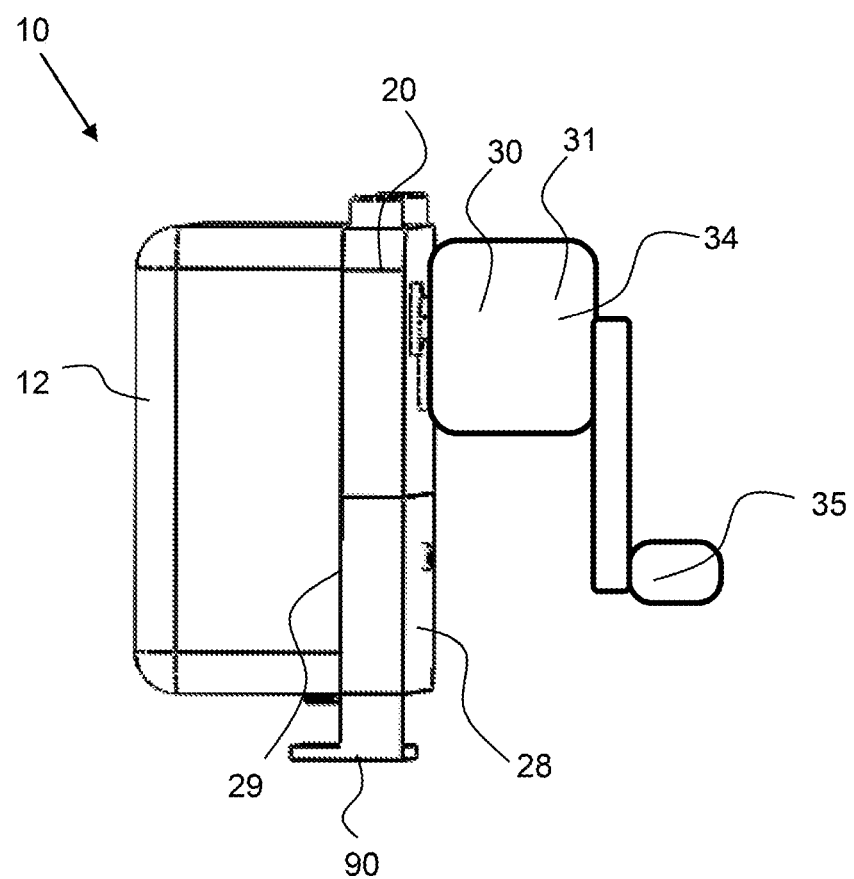
FIG. 5 shows a back view of an exemplary self-propelled cutter having a crank as a drive for the drive input.

As shown in FIG. 5, an exemplary self-propelled cutter 10 has a drive input device 31, such as a crank 34, to provide a drive to the drive input 30. The crank is coupled with the drive input and a handle 35 enables manually driving the gear assembly on the second side 29 of the cutter body 20. A cover 12 is coupled to the cutter body 20 and extends over the gear assembly for safety.

Figure 6:
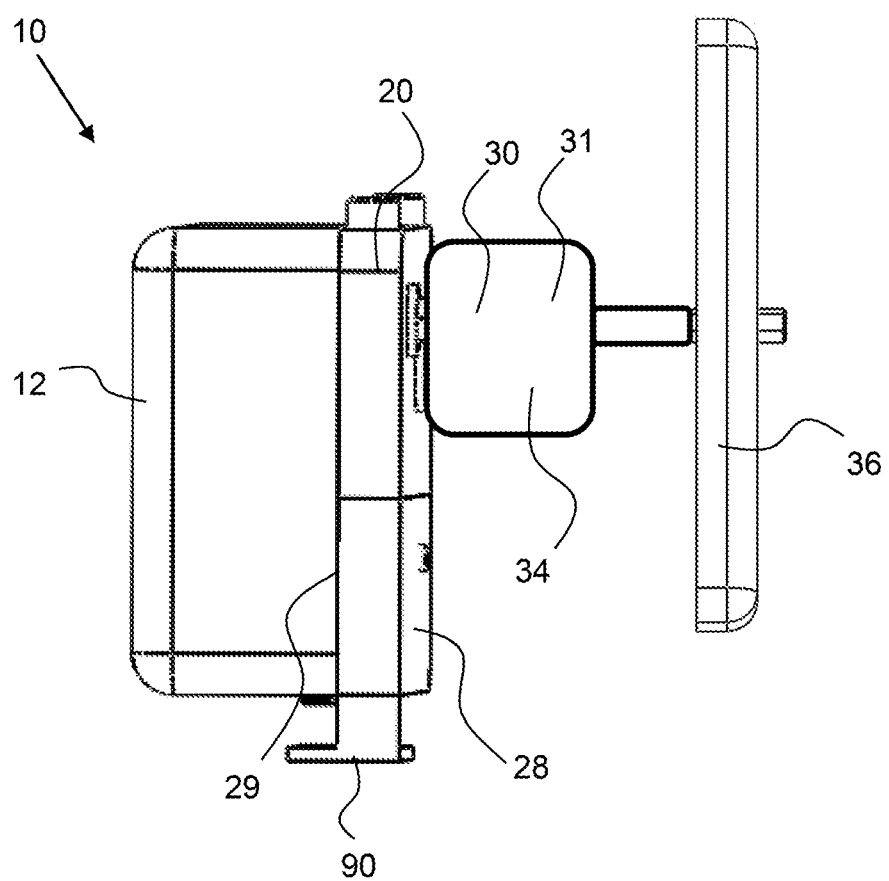
FIG. 6 shows a back view of an exemplary self-propelled cutter having a T-handle as drive for the drive input.

As shown in FIG. 6, an exemplary self-propelled cutter 10 has a drive input device 31, such as a crank 34, to provide a drive to the drive input 30. The crank is coupled with the drive input and a handle 35, a t-handle 36, that enables manually driving the gear assembly on the second side 29 of the cutter body 20. A cover 12 is coupled to the cutter body 20 and extends over the gear assembly for safety.

Figure 7:
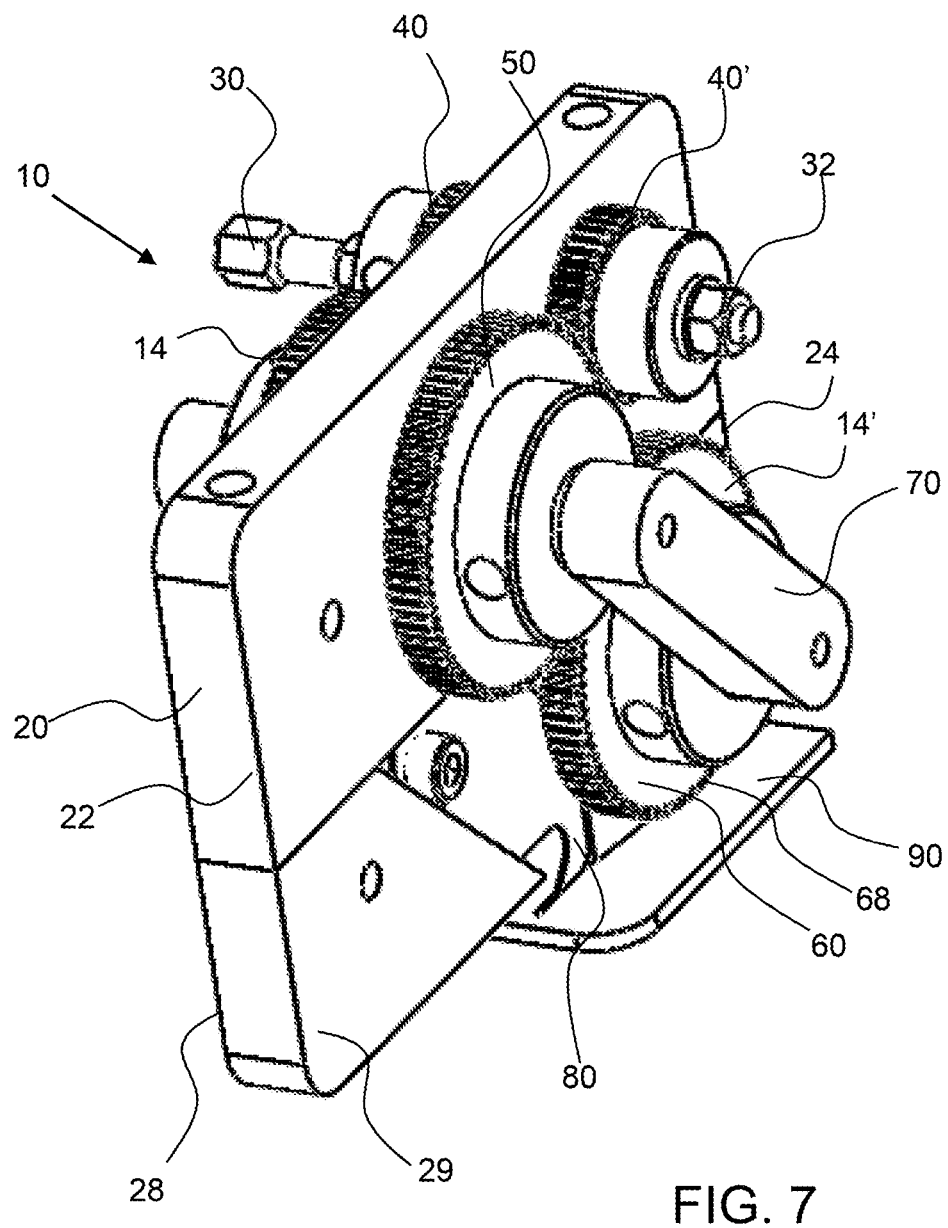
FIG. 7 shows a perspective view of an exemplary self-propelled cutter having a set of gears, or gear assembly, on both the first and second side of the housing body.
Figure 8:
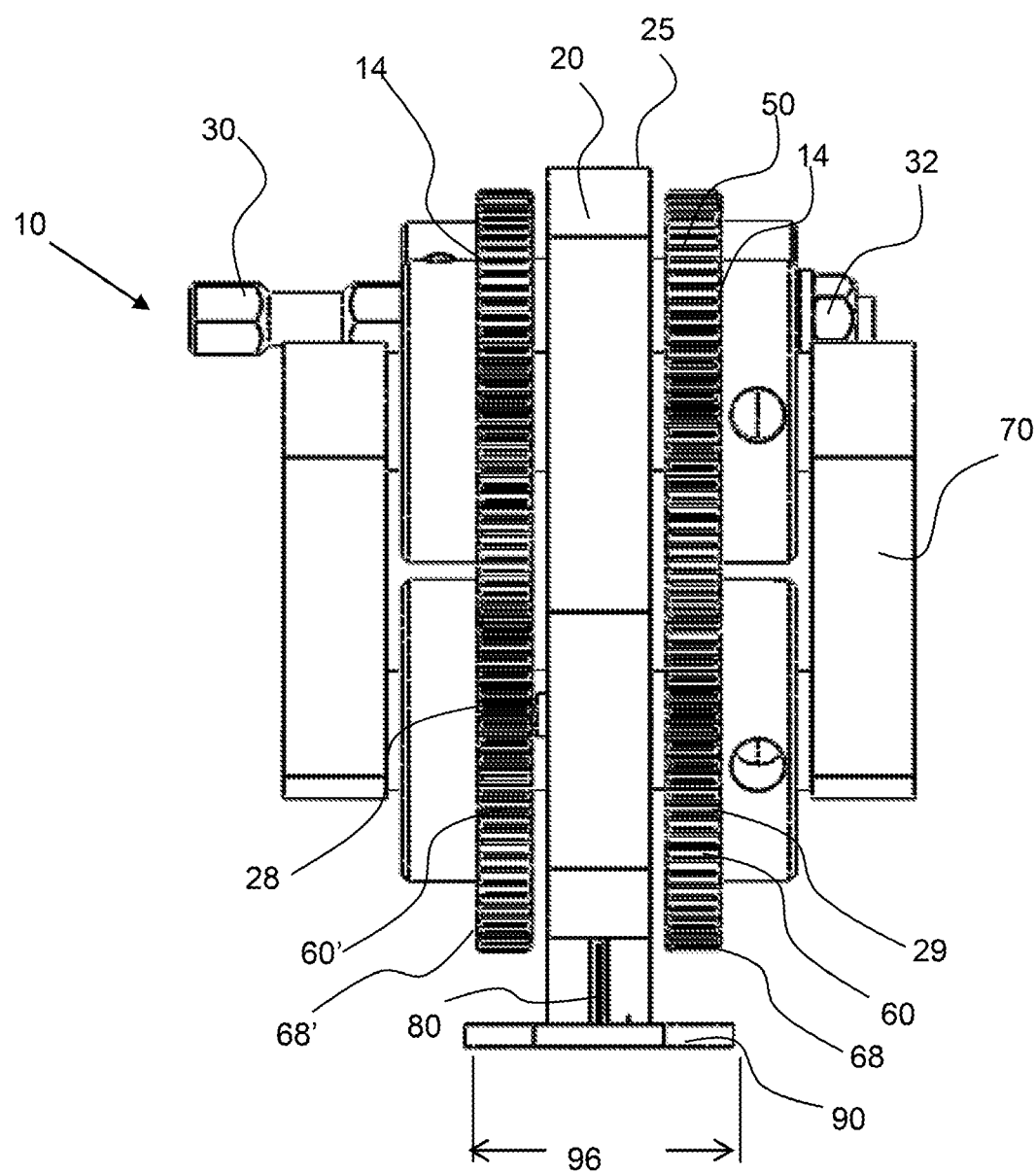
FIG. 8 shows a front view of an exemplary self-propelled cutter having a set of gears, or gear assembly, on both the first and second side of the housing body.

Referring now to FIGS. 7 and 8, an exemplary self-propelled cutter 10 has a gear assembly on both the first side 28 and second side 29 of the housing body 20. A single drive input 30 drives both the first and second drive gears 40, 40', respectively. The second drive gear 40' is driven by the drive input extension 32 that extends from the first side 28 to the second side 29 of the cutter body 20. The dual sided gear assemblies 14, 14', provide two propulsion gears 60, 60' and two treads that may provide for more even and straight propulsion of the cutter 10 with respect to a material. The treads 68, 68' are configured on opposing sides of the fixed blade 80 and rotate down to pinch material against the foot 90 having a width 96.

Figure 9:
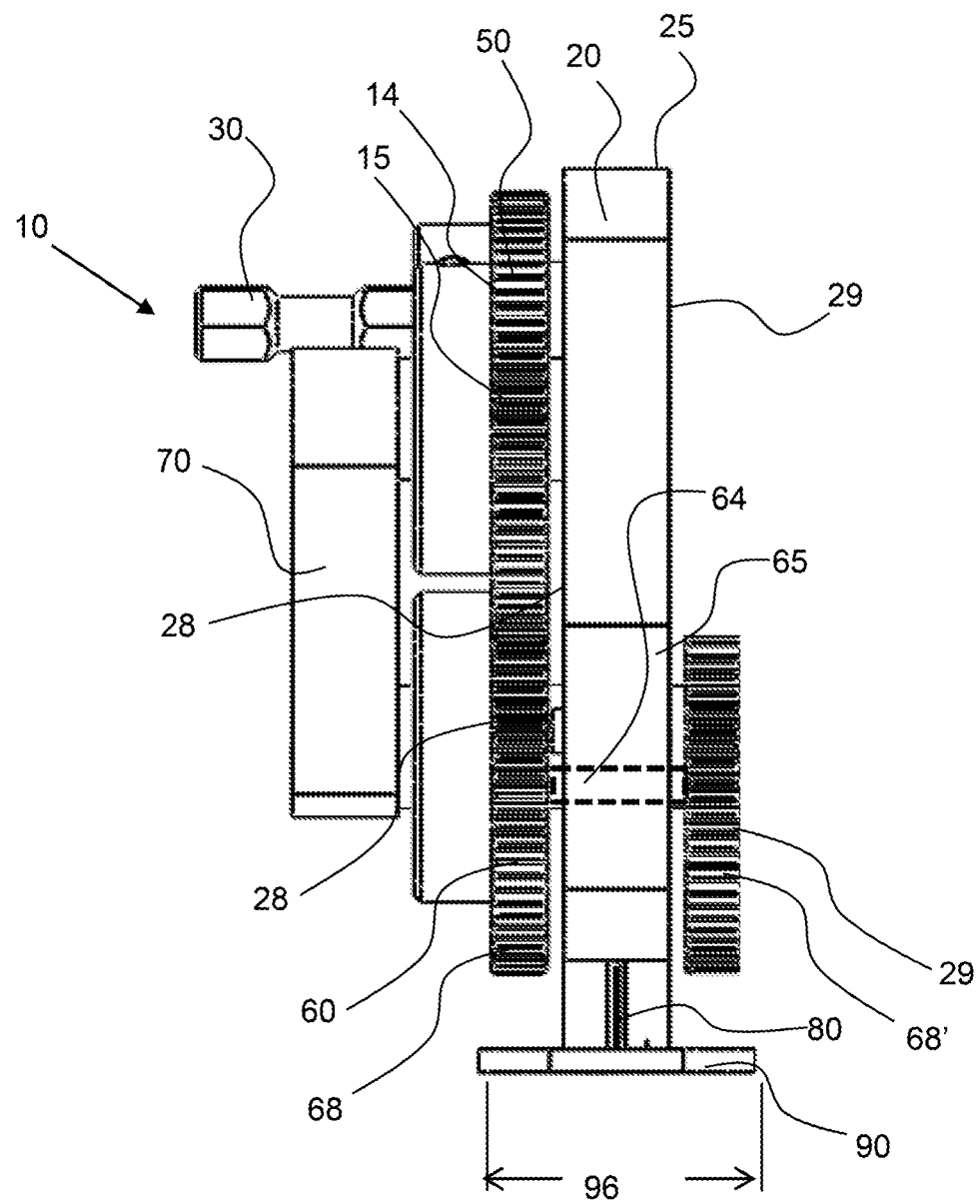
FIG. 9 shows a front view of an exemplary self-propelled cutter having a single gear assembly and a propulsion gear having a propulsion gear extension that extends from a first side of the cutter body to the second side of the cutter body.

As shown in FIG. 9 an exemplary self-propelled cutter 10 has a drive assembly 14 that utilizes a single gear assembly 15 on a first side 28 of the cutter body 20. A propulsion gear 60 is configured on a first side 28 of the cutter body 20 and a propulsion gear extension 64 extends from the first side 28 of the cutter body 20 to the second side 29 of the cutter body 20 through the propulsion gear body recess 65. The propulsion gear extension 64 couples with a second tread 68' on the second side of the cutter body 20. This arrangement enables the first set of gears and the lever arm 70 to move both the first and second treads 68, 68' about the transfer gear 50 as required. The width 96 of the foot 90 is shown in FIG. 9.

Figure 10:
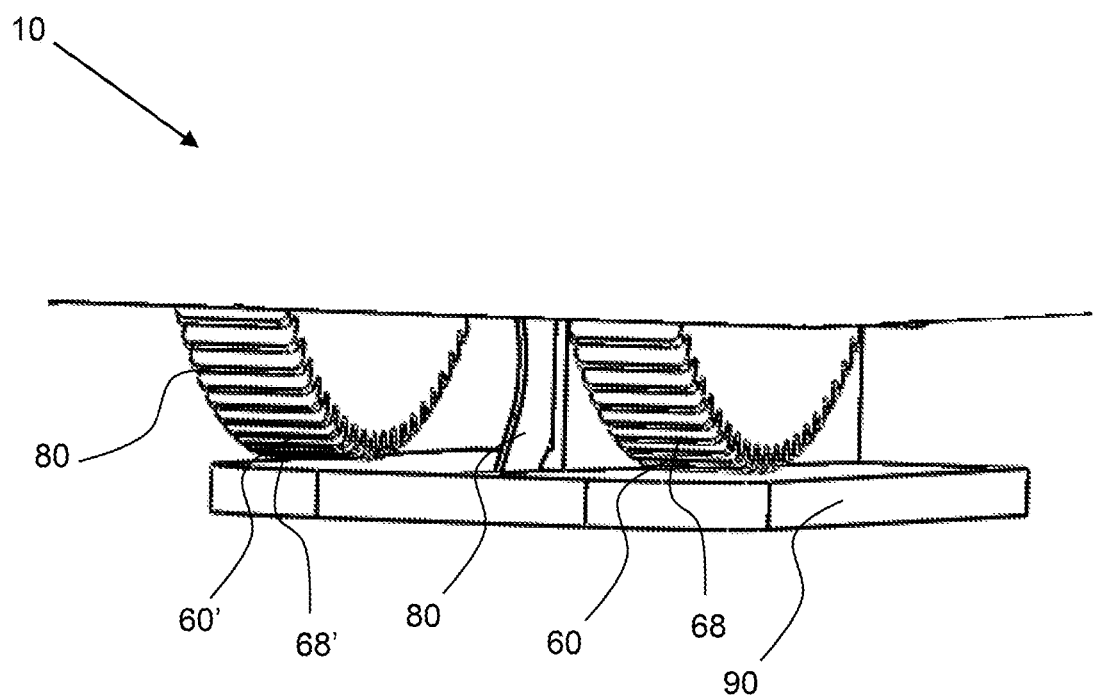
FIG. 10 shows an expanded perspective view of an exemplary self-propelled cutter having two propulsion gears configured on opposing sides of the blade to propel material through the cutter.

As shown in FIG. 10, an exemplary self-propelled cutter 10 has two propulsion gears 60, 60' configured on opposing sides of the fixed blade 80. The propulsion gears 60, 60' rotate about the transfer gear. As described herein, the self-propelled cutter may track more easily in a straight line with treads on either side of the fixed blade 80.

Figure 11:
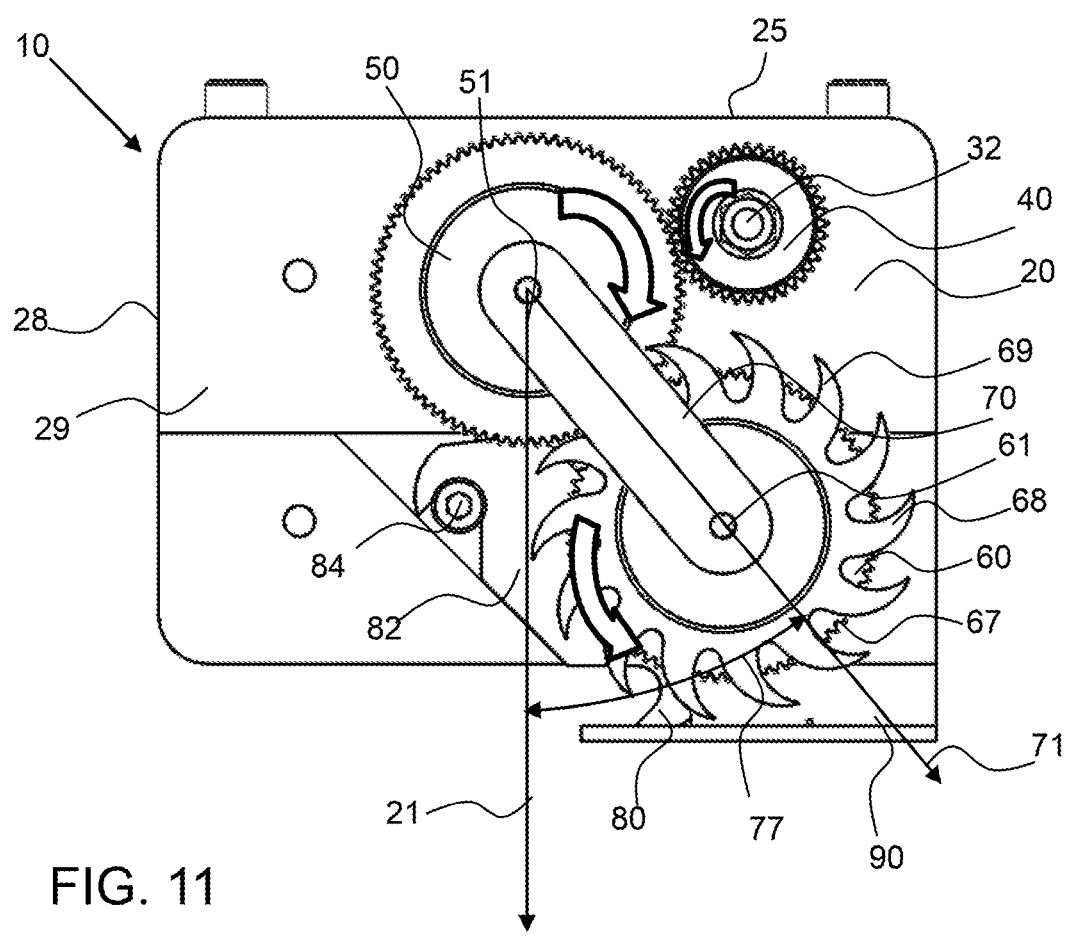
FIG. 11 shows a second side of an exemplary self-propelled cutter having a drive gear engaged with a transfer gear and the transfer engaged with a propulsion gear by a lever arm and a tread extending out from the engagement teeth of the drive gear.

As shown in FIG. 11 an exemplary self-propelled cutter 10 has a tread 68 with propulsion teeth 69 that is coupled with the propulsion gear 60. The propulsion teeth 69 extend out radially from the rotational axis 61 of the propulsion gear a greater distance than the first propulsion engagement teeth 67. The propulsion teeth 69 resemble saw tooth blades having individual portions and having an extended end or point and curved, straight, or radiused sides.

Figure 12:
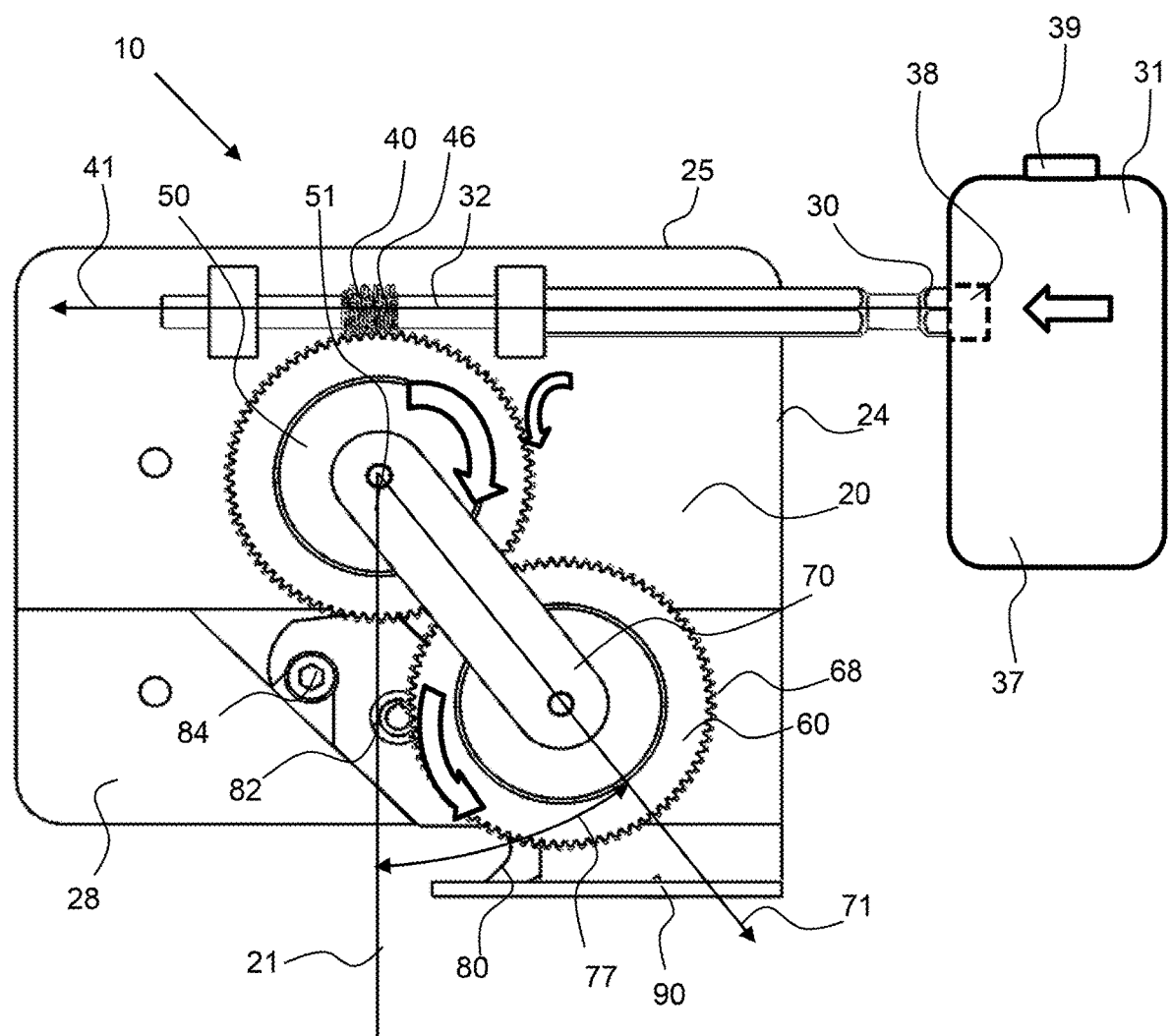
FIG. 12 shows a first side of an exemplary self-propelled cutter having a worm gear engaged with a transfer gear and the transfer engaged with a propulsion gear by a lever arm.
Figure 13:
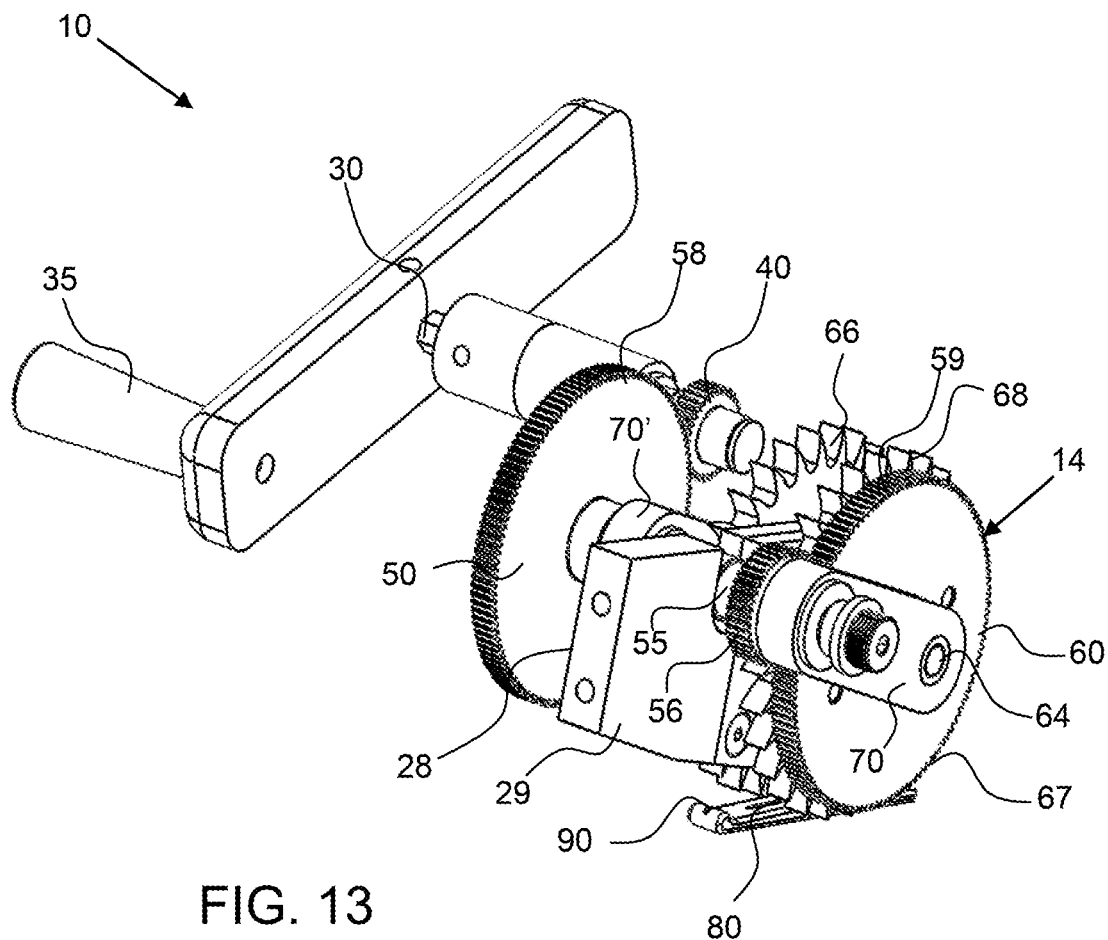
FIG. 13 shows a perspective view of an exemplary self-propelled cutter with the cover removed to expose the internal drive assembly that utilizes a first drive gear driven by the handle and a first transfer gear on a first side or drive side that is coupled with a second transfer gear that drives a second side interface gear, wherein the interface gear is coupled to the second propulsion gear about a propulsion axle.

As shown in FIG. 12, an exemplary self-propelled cutter 10 has a worm gear 46 that engages with the transfer gear 50. The drive input 30 extends to the back 24 of the cutter 10 or cutter body 20. A drive input device can be easily coupled with the drive input 30 to propel the cutter forward. A drive input device 31, such as an electric motor 37 may be coupled with the drive input 30 to turn the drive input extension 32, that has a rotational axis 41 that is orthogonal to the rotational axis 51 of the transfer gear 50, or extends along the length of the cutter body 20. The electric motor may have an input interface 38 such as a socket having planar surfaces to couple with or mate with the planar surfaces on the drive input 30. The electric motor may spin the mating socket to turn the drive input and gear assembly of the cutter 10. The electric motor may have an on/off button 39 to control the movement of the cutter 10 over a material to be cut.

Referring now to FIGS. 13 to 20, an exemplary self-propelled cutter 10 is configured with a drive assembly 14 that couples with a handle 35 and drive input 30. The handle is rotated to rotate the drive input 30 and the first drive gear 40 is attached to the drive input. The first drive gear 40 engages with the first transfer gear 50, both on the first side 28, or drive side of the self-propelled cutter body 10. A transfer gear extension 55 extends as an axle from the first transfer gear 50 to a second transfer gear 56, configured on a second side 29 of the self-propelled cutter body 20, or second side of the fixed blade 80. The second transfer gear 56 engages with a first propulsion gear 60 that drives a propulsion gear extension 64, or axle that drives both the first tread 68, coupled to the first propulsion gear and a second tread 66, configured on a first side 28 of the cutter body 20. The drive assembly is configured with two lever arms 70', 70 on the drive or first side 28 and on the second side 29, respectively. Lever arm 70 extends on the second side 29 from the propulsion gear axle, or propulsion gear extension 64, to the transfer gear extension 55. The lever arm 70' extends on the first side from the propulsion gear extension 64 to the transfer gear extension 55, therefore the two lever arms 70, 70' move in unison to keep the two treads engaged with the material to be cut.

Figure 14:
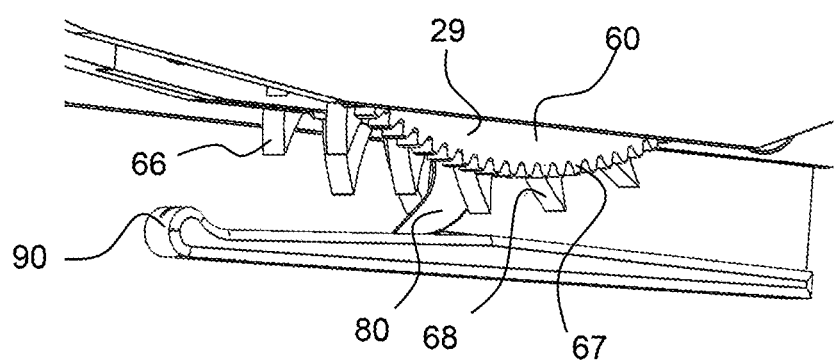
FIG. 14 shows an enlarged perspective view of the foot and blade as well as the propulsion gears.
Figure 15:
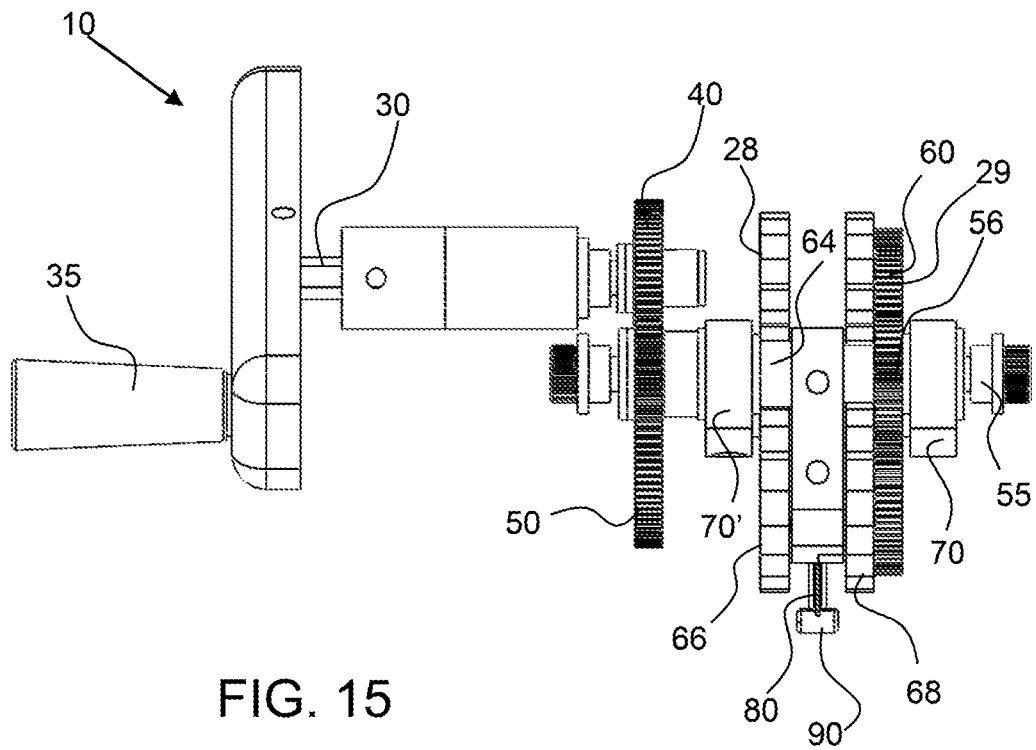
FIG. 15 shows a front view of an exemplary self-propelled cutter with the cover removed to expose the internal drive assembly.
Figure 16:
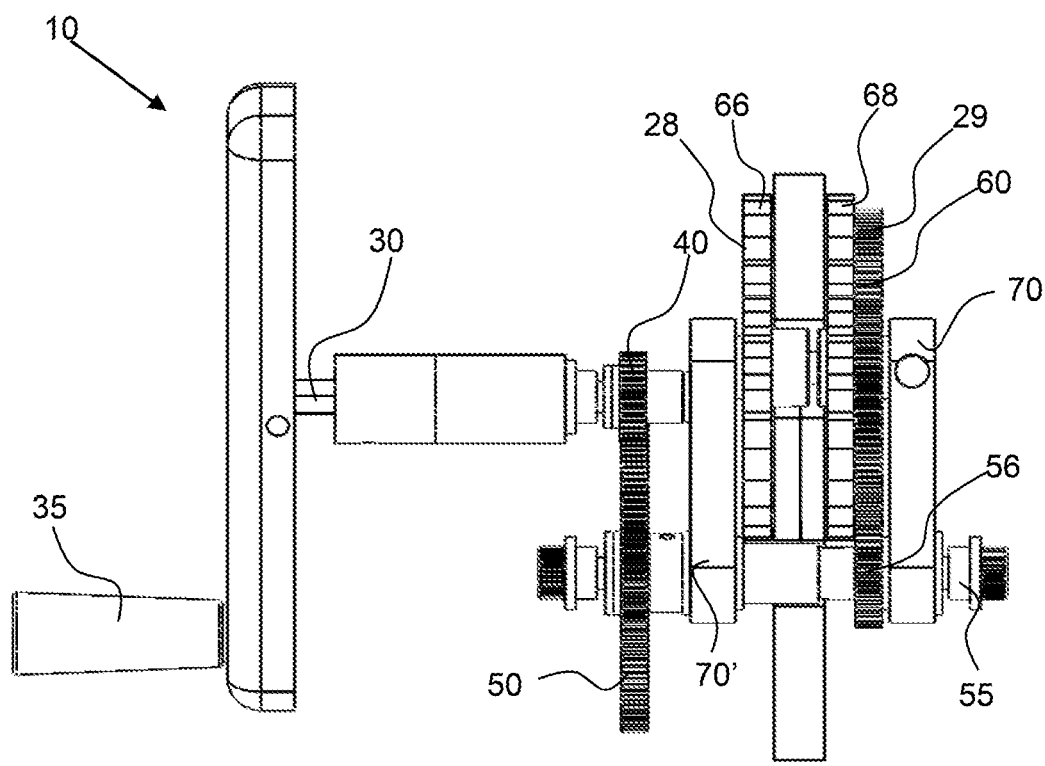
FIG. 16 shows a top view of an exemplary self-propelled cutter with the cover removed to expose the internal drive assembly.

As shown in FIG. 14, the fixed blade 80 is configured between the first tread 68 and the second tread 66.

Figure 17:
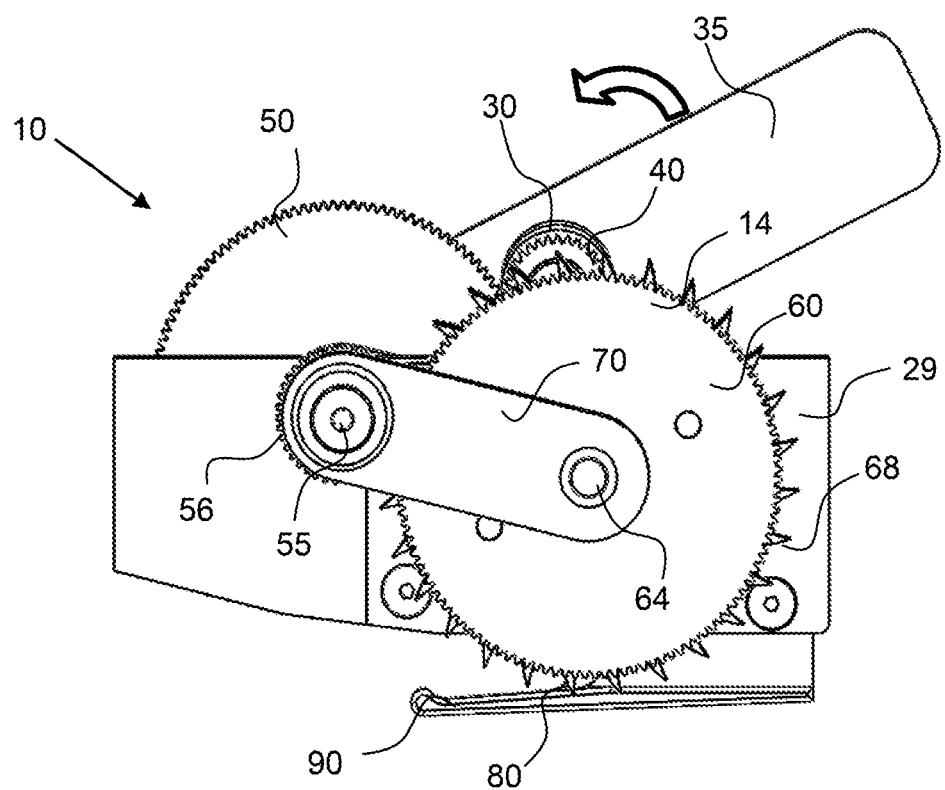
FIG. 17 shows a second side view of an exemplary self-propelled cutter with the cover removed to expose the internal drive assembly; the propulsion gear is down in a drive configuration.
Figure 18:
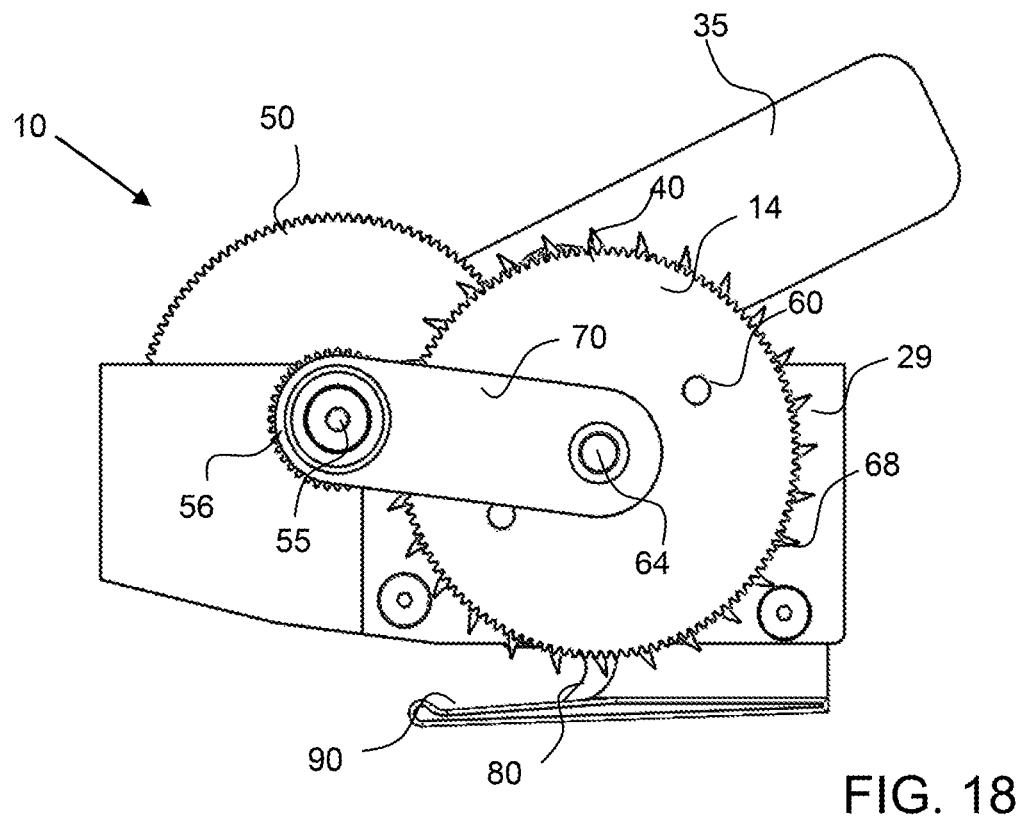
FIG. 18 shows a second side view of an exemplary self-propelled cutter with the cover removed to expose the internal drive assembly; the propulsion gear is up as the handle is not being turned.

As shown in FIG. 17, the exemplary drive assembly 14 is in a down and drive configuration and the handle 35 is being turned to pivot the lever arm 70 as indicated by the bold curved arrow. The lever arm 70 is pivoted down to engage a material being fed over the foot and into the cutter 10. As shown in FIG. 18, the tread 68 is up from the foot 90 and the lever arm 70 is pivoted up.

Figure 19:
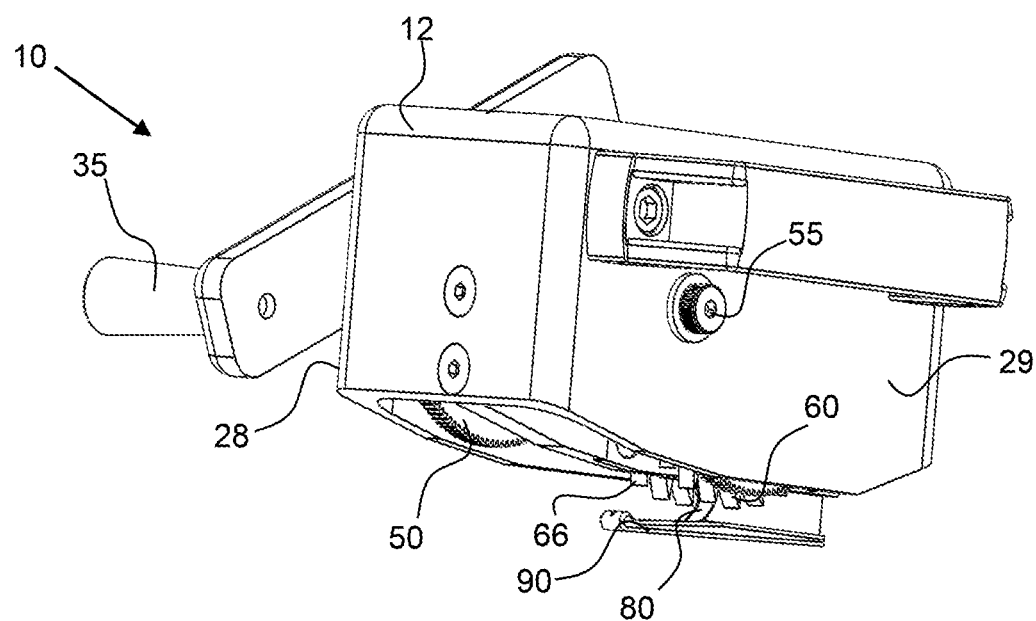
FIG. 19 shows a perspective view of an exemplary self-propelled cutter.

FIG. 19 shows the self-propelled cutter 10 shown in FIGS. 13-18 and 20-21 with the cover 12 configured thereon.

Figure 20:
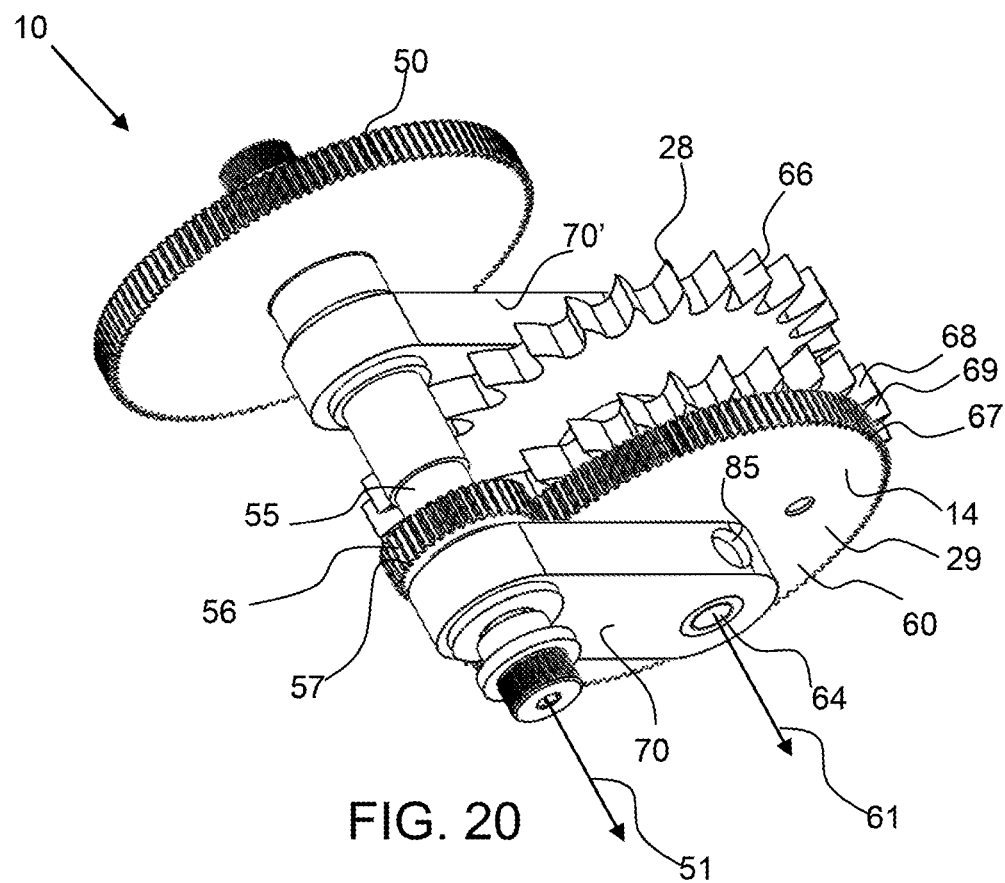
FIG. 20 shows a perspective view of an exemplary drive assembly configured in the exemplary self-propelled cutter shown in FIGS. 13 to 19.
Figure 21:
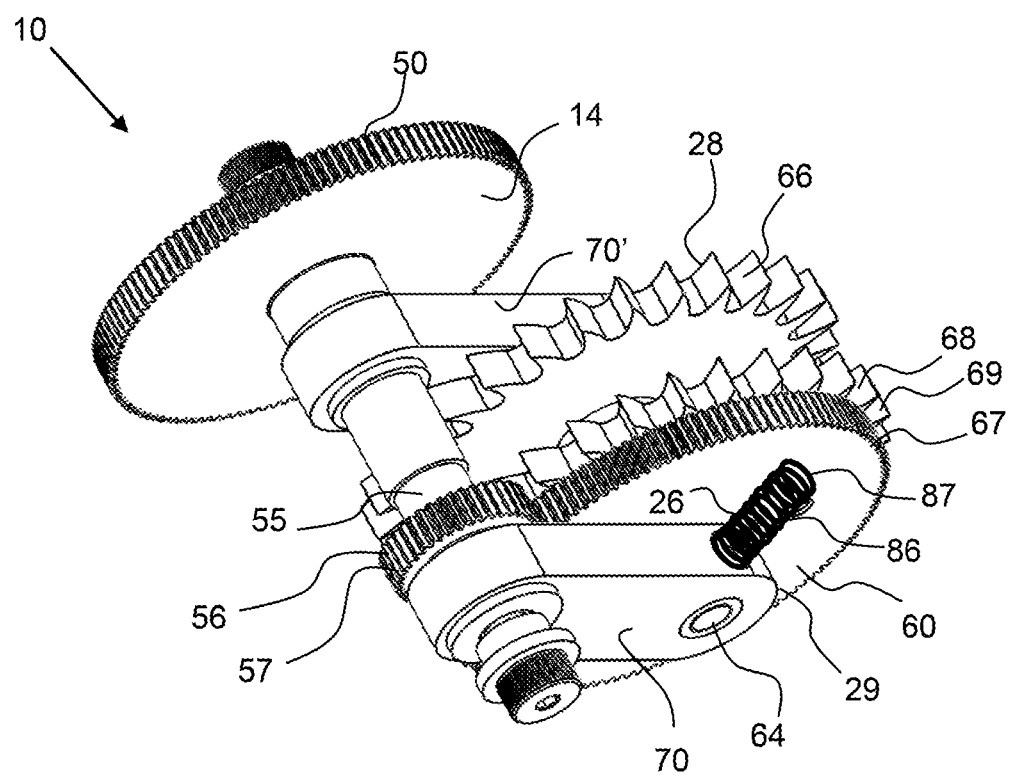
FIG. 21 shows a perspective view of an exemplary drive assembly shown in FIG. 20 with a spring configured in the spring recess.

Referring now to FIGS. 20 and 21, an exemplary drive assembly 14 comprises a first transfer gear 50 that is on a first side, or drive input side, of the cutter body, (not shown), a transfer gear extension 55 that extends to a second transfer gear 56, on a second side of the cutter body. The second transfer gear 56 engages with the first propulsion gear 60 through the gear teeth 57 of the second transfer gear 56 engaging with the engagement teeth 67 of the first propulsion gear. A tread 68 is coupled with the first propulsion gear and has propulsion teeth that extend radially out beyond the engagement teeth 67 of the first propulsion gear. The lever arm 70 is coupled between the first propulsion gear and the second transfer gear 56, and holds these two gears in engagement. The lever arm 70 pivots around the transfer gear extension 55, or rotation axis 51 of the second transfer gear 56, and the propulsion gear extension 64, or rotational axis of the propulsion gear 61. A spring receiver recess 85 is shown in the lever arm 70 in FIG. 20, and a spring 86 is configured in the spring recess in FIG. 21. The spring extends from the spring recess to an extended end 87 of the spring that is configured to interface with the housing or cover to provide a spring force on the lever arm 70 and to act as a back-stop 26 for the lever arm 70, thereby preventing the lever arm 70 from rotating up about the propulsion transfer gear rotation axis 51.

Figure 22:
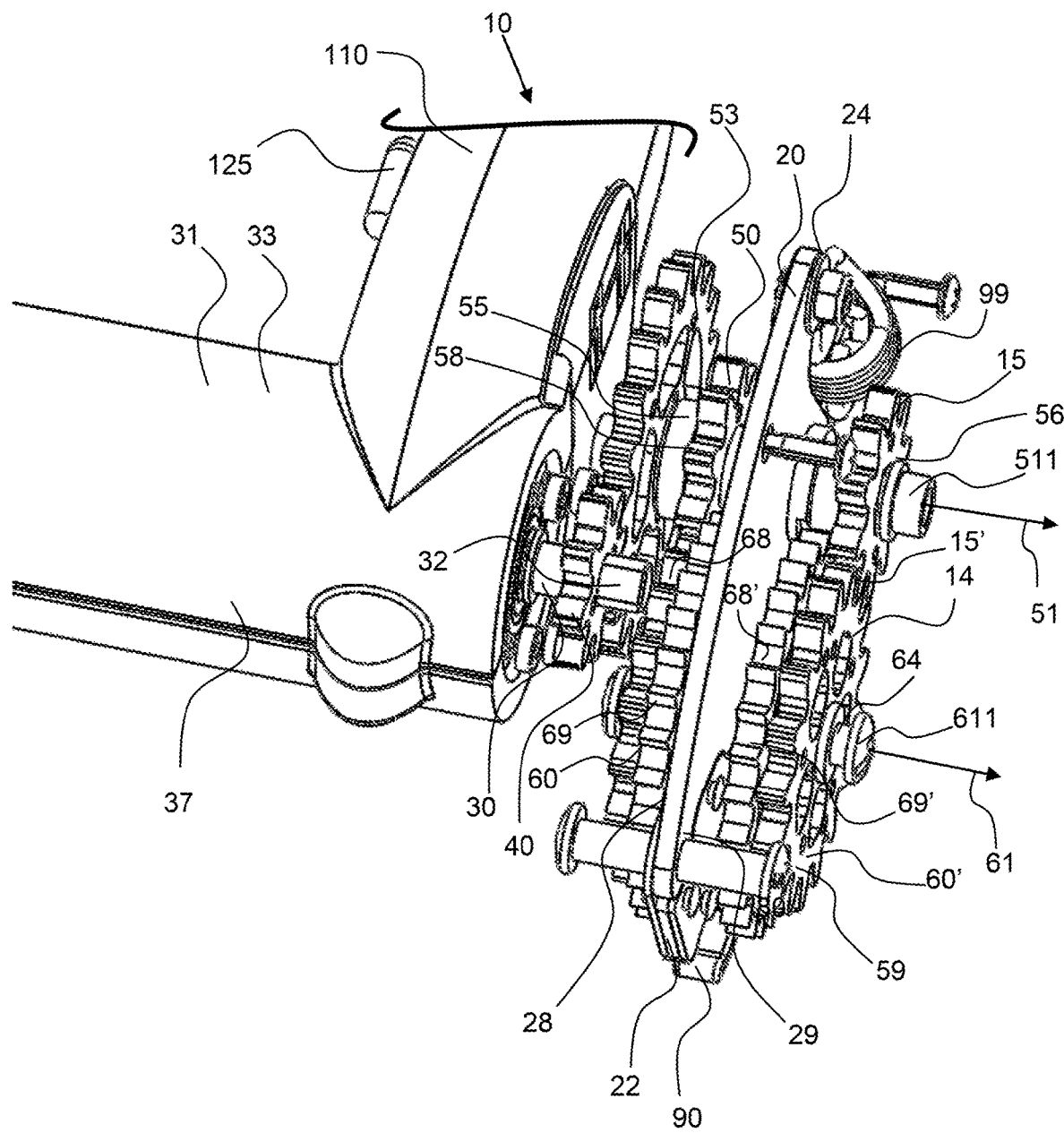
FIG. 22 shows a perspective view of an exemplary self-propelled cutter with the cover removed from the cutter body to show the gear assembly.
Figure 23:
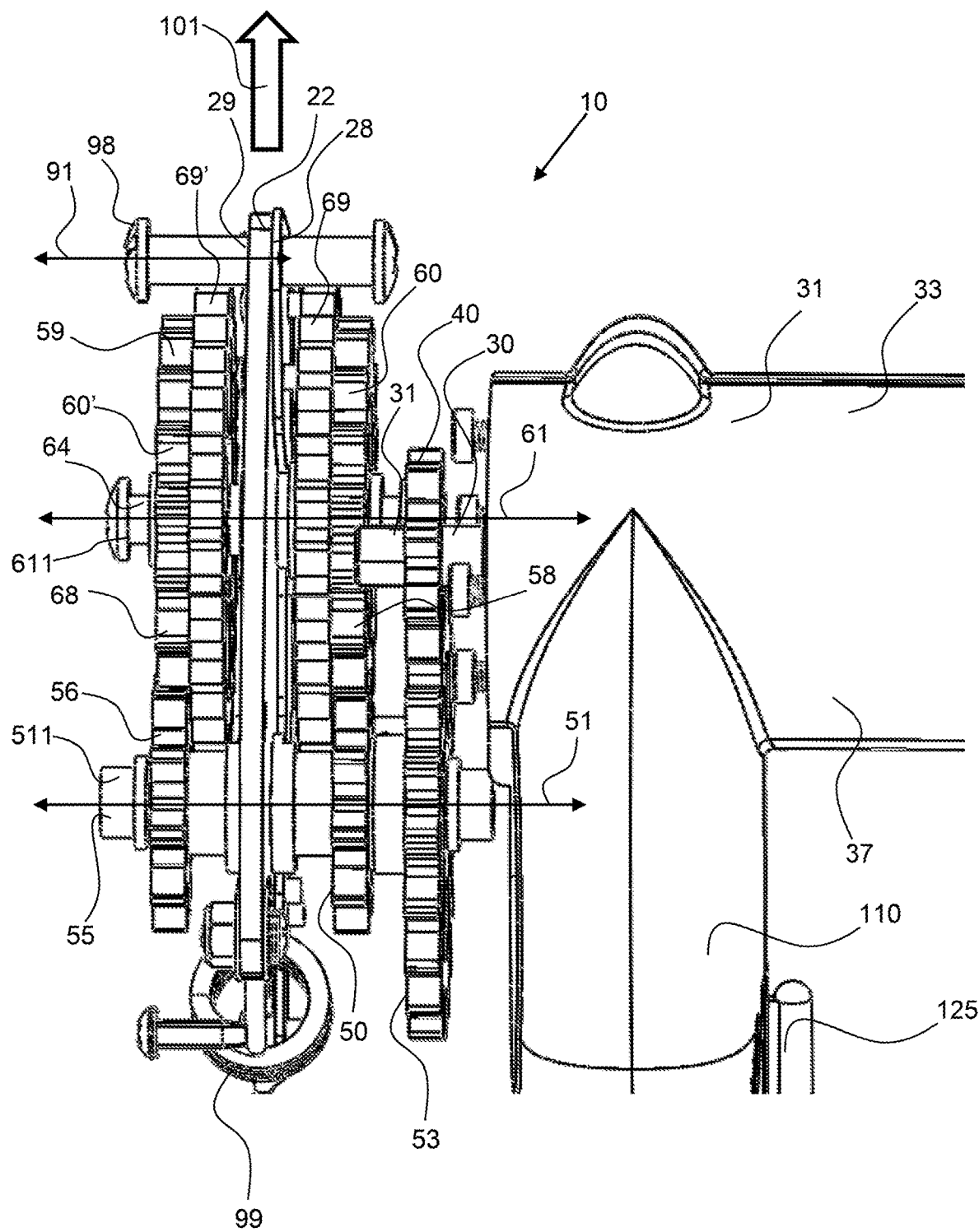
FIG. 23 shows a perspective view of an exemplary self-propelled cutter with the cover removed from the cutter body to show the gear assembly.

Referring now to FIGS. 22 to 29, an exemplary self-propelled cutter is configured with a drive input device 31, such as an electric motor 37, that is powered to automatically drive the drive input 30 which then turns the gear assembly 15 and ultimately the two propulsion gears 60, 60'. The drive input 30, such as the electric motor 37, may be configured in a drive housing 33 which may extend orthogonally from the length of the cutter body 20, or orthogonal to the direction of cutting 101. A first gear assembly 58 is configured on a first side 28 of the cutter body and a second gear assembly 59 is configured on a second side 29 of the cutter body. As shown in FIGS. 22 and 23, the drive input extension 32 extends from the drive input device 31, an electric motor 37 and has a drive gear 40 coupled to the drive input extension 32. The drive gear 40 meshes with an interface transfer gear 53 on the first side 28 of the cutter body 20. The interface transfer gear 53 has a transfer gear extension 55 that extends along the rotational axis 51 of the interface transfer gear 53. A first transfer gear 50 on the first side 28 of the cutter body 20 and a second transfer gear 56 on the second side 29 of the cutter body 20 are coupled to the transfer gear extension 55, a transfer gear axle 511, and are rotated about the transfer gear rotational axis 51, by the attachment to the transfer gear extension 55. The first transfer gear 50 on the first side 28 of the cutter body 20 meshes with a first propulsion gear 60 to turn the first propulsion teeth 69, or tread 68 and the second transfer gear 56 on the second side 29 of the cutter body 20 meshes with the second propulsion gear 60' to turn the second propulsion teeth 69', or tread 68'. The first and second propulsion gears and the respective propulsion gear teeth may be coupled together by a propulsion gear extension 64 that extends through the cutter body 20 along the rotational axis 61 of the propulsion gears to form a propulsion axle 611. The gear size and ratio of the first and second transfer gears and propulsion gears may be the same to effectively drive the first and second propulsion teeth at the same speed.

Figure 24:
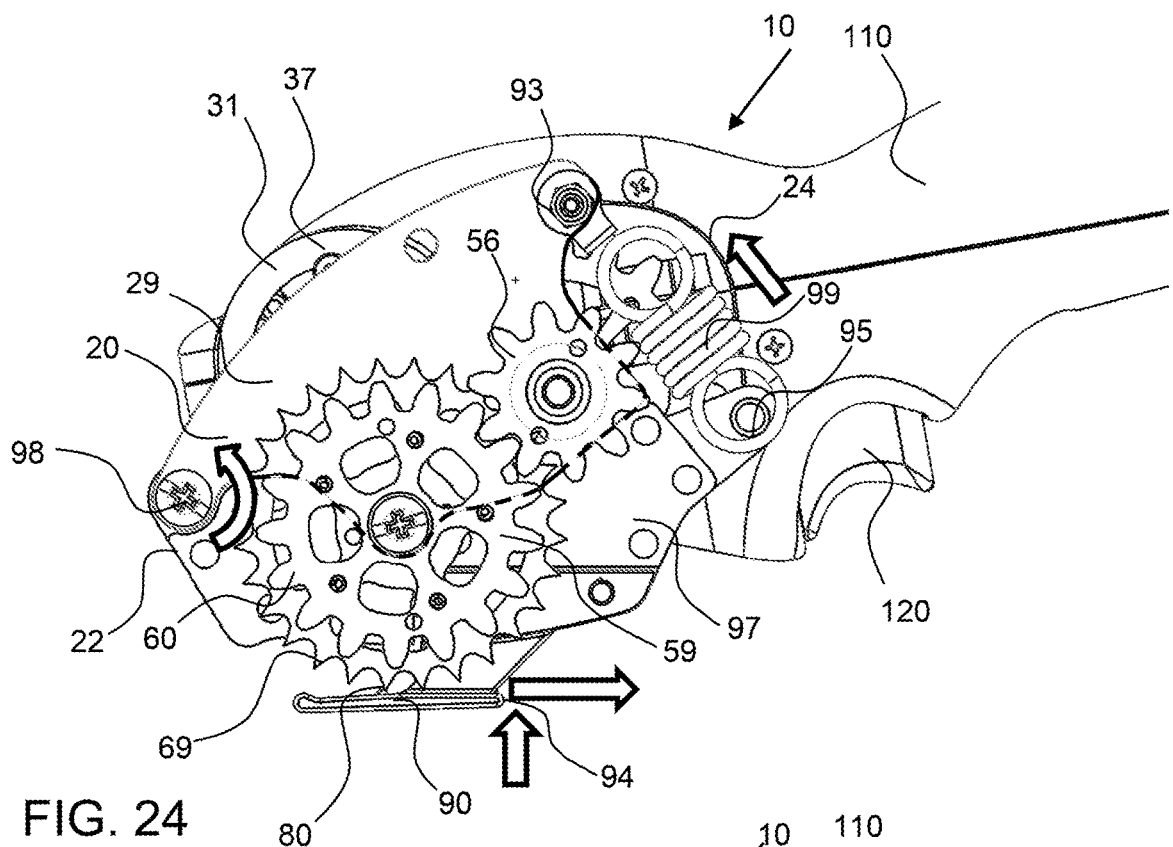
FIG. 24 shows a second side view of an exemplary self-propelled cutter with the cover removed from the cutter body to show the gear assembly and the foot spring coupled to the foot pivot plate to pivot the foot up.
Figure 25:
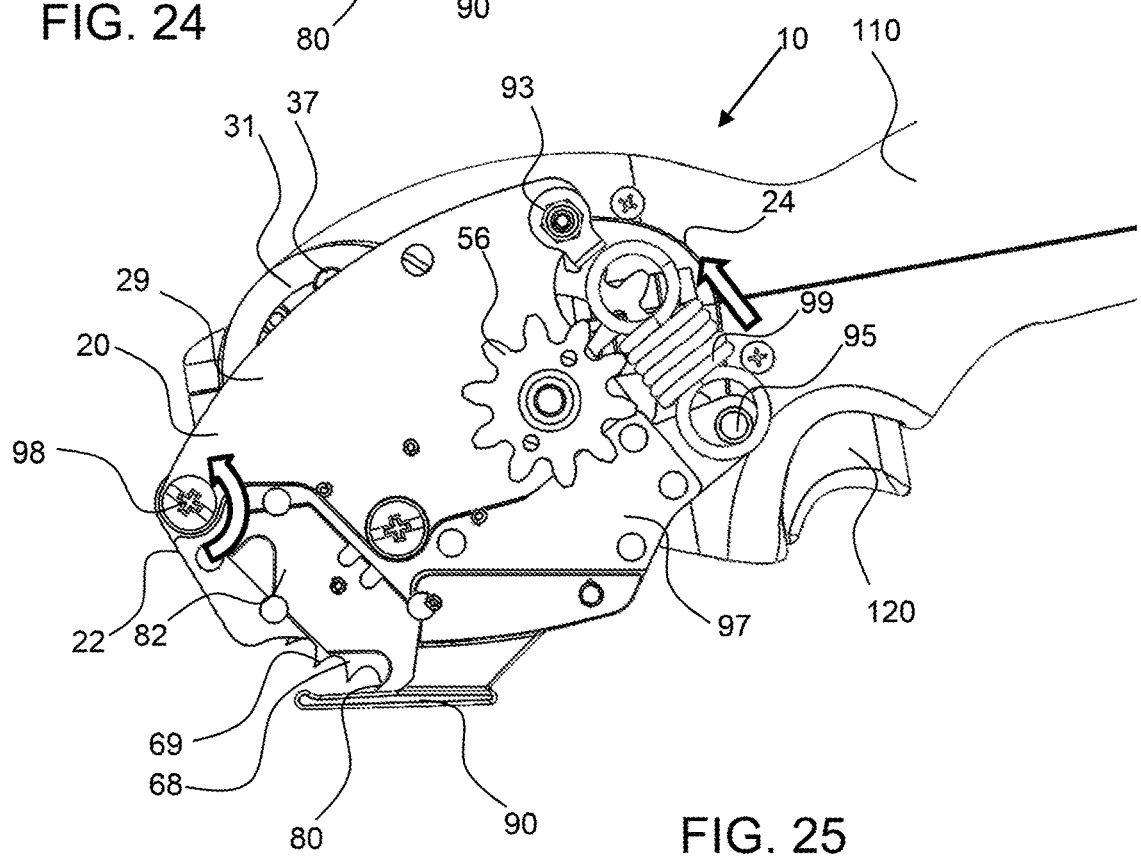
FIG. 25 shows a second side view of an exemplary self-propelled cutter with the cover removed from the cutter body to show the gear assembly and the foot spring coupled to the foot pivot plate to pivot the foot up.
Figure 26:
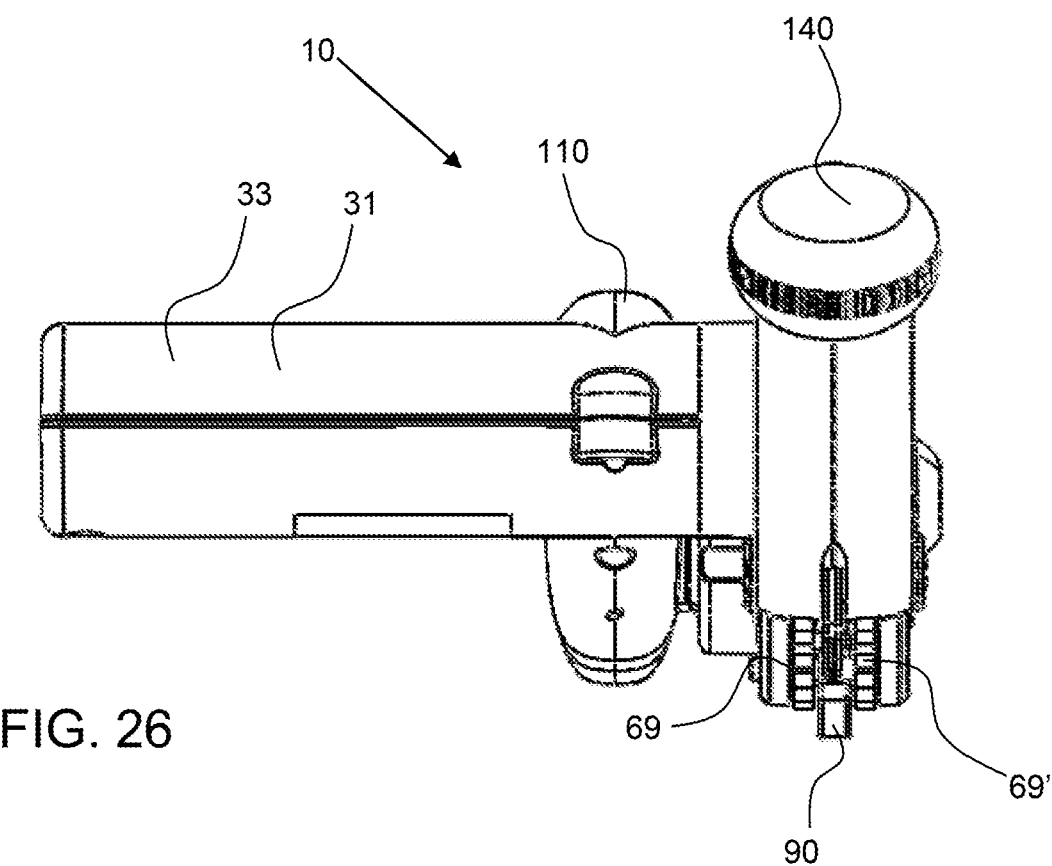
FIG. 26 shows a front view of the exemplary self-propelled cutter shown in FIGS. 22 to 25 with the cover configured over the cutter body.
Figure 27:
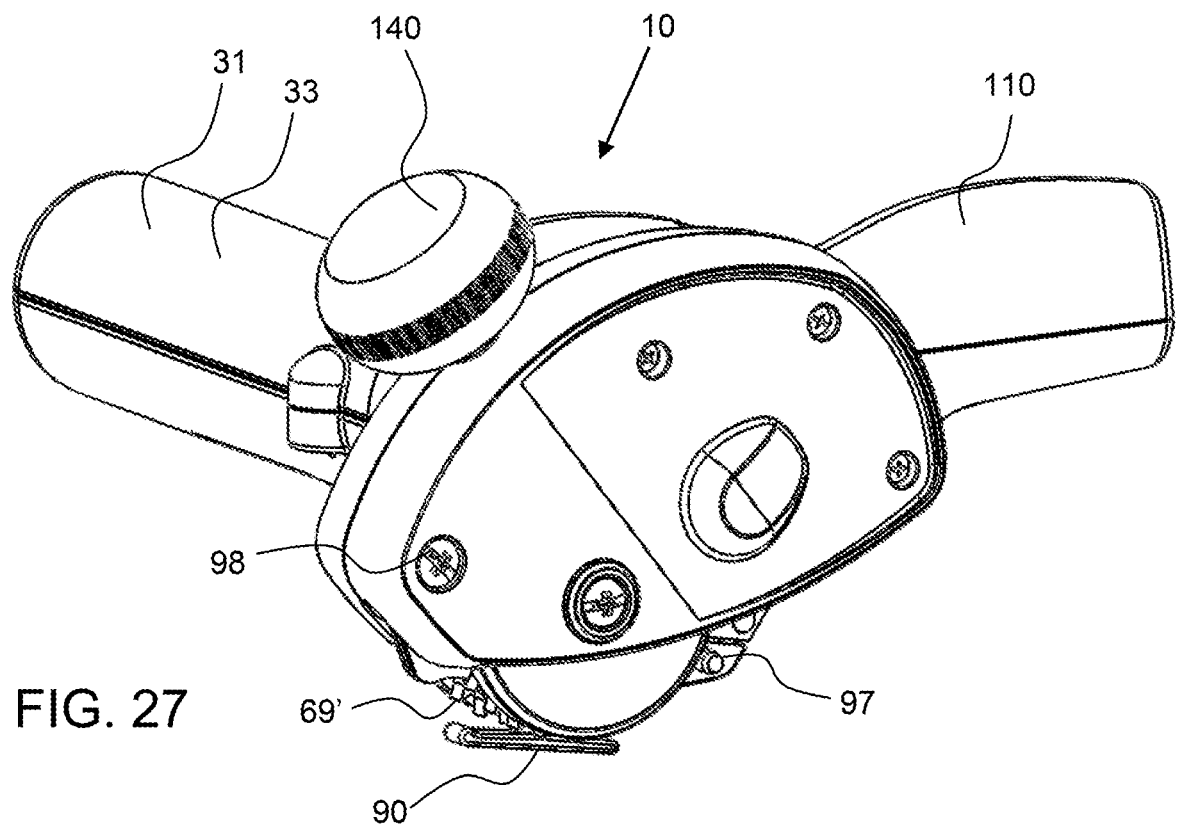
FIG. 27 shows a second side perspective view of the exemplary self-propelled cutter shown in FIGS. 22 to 25 with the cover configured over the cutter body.

As shown in FIGS. 24 and 25, the foot 90 may be coupled to a foot pivot plate 97 that is configured to pivot about a foot pivot 98 to keep the foot rotated up toward the cutter body 20. The foot pivot 98 is configured forward, or more proximal to the front 22 of the cutter body than the foot 90 and the spring 99 is configured back from the foot 90 or more proximal to the back 24 of the cutter body. The foot may be pivoted away from the cutter body to accommodate thicker material being fed over the foot and cut by the fixed blade 80. The foot plate 97 pivots about the foot pivot axis 91, shown in FIG. 23. The spring 99 is coupled to the cutter body by a foot-spring body attachment 93 and to the foot 90 by a foot-spring plate attachment 95, such as a post extending from the foot pivot plate 9.

Referring now to FIGS. 26 to 29, an exemplary self-propelled cutter 10 has an input drive device 31 that is coupled to the cutter body 20 and configured to automatically drive the gear assembly and the propulsion teeth 69, 69' to pull material over the foot 90 and across the blade fixed 80 to cut the material. The drive input device is an electric motor 37 configured in a drive housing 33 that extends orthogonally to the direction of cutting or the length of the cutter body 20 extending from the front to the back of the cutter body. The exemplary self-propelled cutter 10 has a handle 110 and an activator button 120 that activates the input drive device 31 when activated. An additional handle 140 is provided to enable applying additional force as material is cut using the propelled cutter 10. The combination of the dual sided tread configured on opposing sides of the cutter body 20 and the foot spring 99 pulling the foot 90 up toward the cutter body provides effective force between the foot and the blade to ensure the material is cut while the tread 68 effectively translates the material over the foot 90 and fixed blade 80, as indicated by the two bold arrows proximal the trailing end 94 of the foot 90 in FIG. 24.

Figure 28:
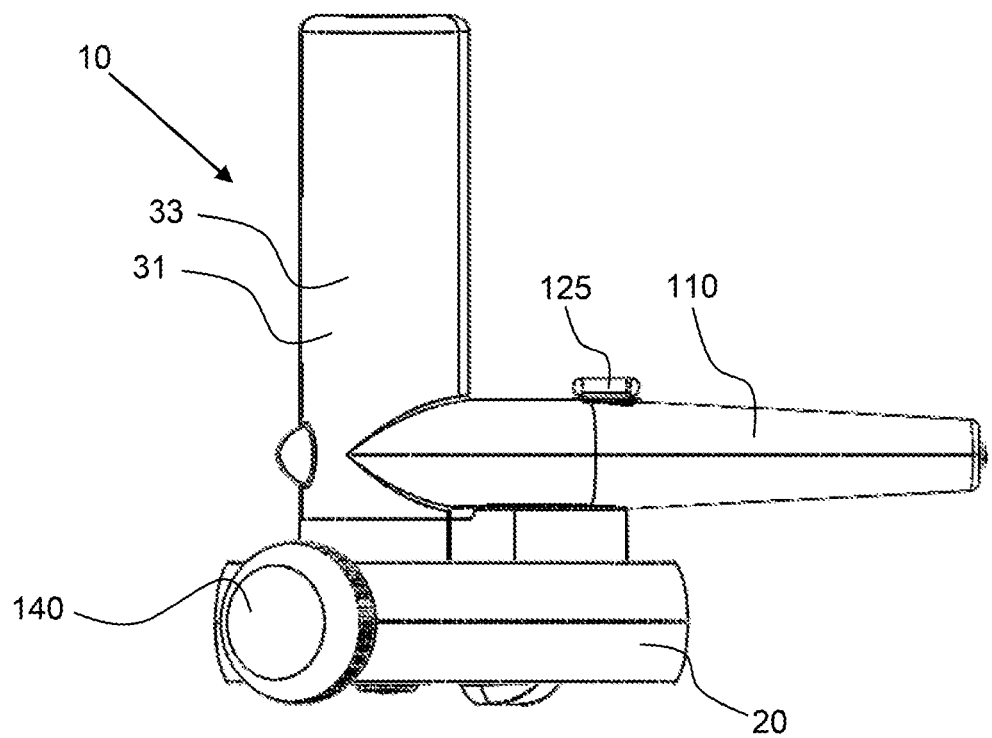
FIG. 28 shows a top view of the exemplary self-propelled cutter shown in FIGS. 22 to 25 with the cover configured over the cutter body.
Figure 29:
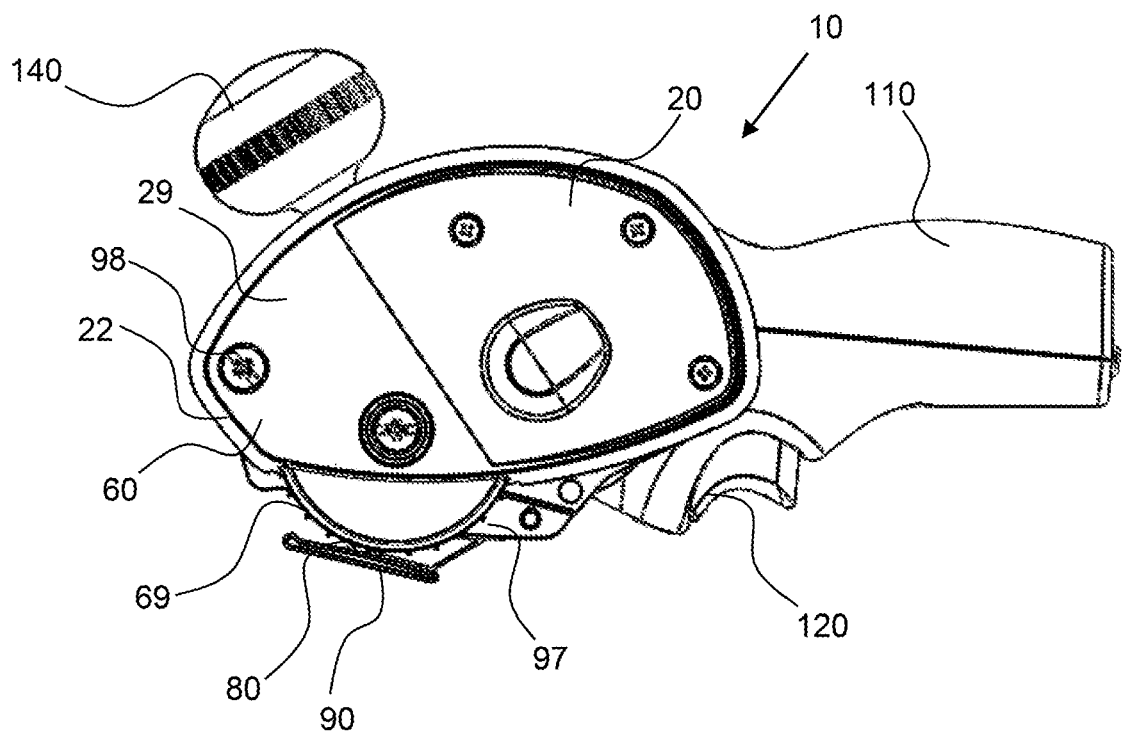
FIG. 29 shows a second side view of the exemplary self-propelled cutter shown in FIGS. 22 to 25 with the cover configured over the cutter body.

As shown in FIG. 28, a directional switch 125 is configured on the handle 110 to allow a user to change the direction of rotation of the propulsion teeth.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A propelled cutter comprising:
   a) a cutter body comprising:
      i) a first side; and
      ii) a second side;
      iii) a front;
      iv) a back;
      v) a bottom;
      vi) a top; and
      vii) a vertical axis extending from said bottom to said top when in an upright position;
   b) a fixed blade coupled to the cutter body;
   c) a foot extending from said bottom of the cutter body and configured to guide a material to be cut over the foot and across the fixed blade;
   d) a drive input device coupled with a drive input extension that is coupled with the cutter body and with a drive assembly, said drive assembly comprising:
      iii) a first propulsion gear configured on the first side of the cutter body and having a rotational axis;
      iv) a first transfer gear configured on the first side of the cutter body and having a rotational axis and being movably attached and movably engaged with the first propulsion gear to spin the first propulsion gear;
      v) a second propulsion gear configured on the second side of the cutter body and having a rotational axis;
      vi) a second transfer gear configured on the second side of the cutter body and having a rotational axis and being movably attached and movably engaged with the second propulsion gear to spin the second propulsion gear;

wherein the first propulsion gear is driven by the first transfer gear to spin to move said material to be cut across the fixed blade to cut said material; and wherein the second propulsion gear is driven by the second transfer gear to spin to move said material to be cut across the fixed blade to cut said material.

2. The propelled cutter of claim 1, further comprising:

a foot pivot plate, wherein the foot is coupled to the foot pivot plate;

a foot spring coupled to the foot pivot plate and to the cutter body to apply a force on the foot pivot plate; and a foot pivot, wherein said force of the foot spring creates a moment force about the foot pivot to rotate the foot pivot plate about the foot pivot.

3. The propelled cutter of claim 2, wherein the foot pivot is configured more proximal to the front of the cutter body than the foot and wherein the foot spring is configured more proximal to the back of the cutter body than the foot.

4. The propelled cutter of claim 2, wherein the spring is a coiled spring.

5. The propelled cutter of claim 1, wherein the first propulsion gear and the second propulsion gear rotate about the same rotational axis.

6. The propelled cutter of claim 5, wherein a propulsion gear extension extends through the cutter body and wherein the first propulsion gear and the second propulsion gear are coupled to said propulsion gear extension.

7. The propelled cutter of claim 1, wherein the first transfer gear and the second transfer gear rotate about the same rotational axis.

8. The propelled cutter of claim 7, wherein a transfer gear extension extends through the cutter body, and wherein the first transfer gear and the second transfer gear are coupled to said transfer gear extension.

9. The propelled cutter of claim 1, wherein the foot extends forward the fixed blade.

10. The propelled cutter of claim 1, wherein the fixed blade is detachably attachable to the cutter body.

11. The propelled cutter of claim 1, wherein the first propulsion gear and the second propulsion gear each comprise a tread that extends radially outward around an outer diameter of the first propulsion gear and second propulsion gear respectively to engage with said material to move said material.

12. The propelled cutter of claim 1, wherein the drive assembly further comprises a first drive gear that is coupled with the drive input and wherein the first drive gear is on the first side of the cutter body having the drive input.

13. The propelled cutter of claim 12, further comprising an interface gear that is configured between and meshes with both the first drive gear and the first transfer gear.

14. The propelled cutter of claim 1, wherein the drive input device is an electric motor.

15. The propelled cutter of claim 14, wherein the cutter body further comprising a drive housing and wherein the electric motor is coupled to and configured in said drive housing.

16. The propelled cutter of claim 15, wherein the drive housing extends orthogonal from a length of the cutter body extending from the front to the back of the cutter body.

17. The propelled cutter of claim 15, further comprising a handle coupled to and extending from the drive housing and further comprising an activator button configured on the handle and coupled to the electric motor and configured to activate the electric motor.

* * * * *